United States Patent [19]

Anthony et al.

[11] Patent Number: 5,145,954
[45] Date of Patent: Sep. 8, 1992

[54] DERIVATIVES OF ALPHAPHENYLACRYLIC ACID AND THEIR USE IN AGRICULTURE

[75] Inventors: Vivienne M. Anthony, Maidenhead; John M. Clough, Marlow; Paul DeFraine, Wokingham; Christopher R. A. Godfrey, Bracknell; Thomas E. Wiggins, Bracknell; David J. Tapolczay, Bracknell, all of England

[73] Assignee: Imperial Chemical Industries PLC, London, England

[21] Appl. No.: 39,458

[22] Filed: Apr. 17, 1989

[30] Foreign Application Priority Data

Apr. 17, 1986 [GB] United Kingdom ............... 8609455

[51] Int. Cl.$^5$ ............... C09B 29/01; C09B 29/02; C09B 29/34; C07C 149/40
[52] U.S. Cl. ............... 534/852; 546/248; 546/238; 548/526; 560/15; 544/179; 544/182; 544/215; 544/332; 544/335; 549/43; 549/79; 549/388; 549/461; 549/501; 71/88; 71/91; 71/92; 71/93; 71/94; 71/95; 71/107
[58] Field of Search ............... 534/852; 560/15; 548/526; 546/248, 238; 544/179, 182, 215, 332, 335; 549/43, 79, 388, 461, 501

[56] References Cited

U.S. PATENT DOCUMENTS

| | | | |
|---|---|---|---|
| 2,940,992 | 6/1960 | Zaugg et al. | 560/15 |
| 3,281,455 | 10/1966 | Steinberg | 560/15 X |
| 3,503,954 | 3/1970 | Gies | 534/852 X |
| 3,681,432 | 1/1972 | Nelson | 260/473 F |
| 3,789,064 | 1/1974 | Hechenbleikner et al. | 560/15 X |
| 3,828,033 | 8/1974 | Nelson | 560/15 X |
| 3,828,091 | 8/1974 | Strong | 260/465 F |
| 4,101,543 | 7/1978 | Stiot et al. | 534/852 X |
| 4,242,519 | 12/1980 | Tsuchihashi et al. | 560/15 |
| 4,709,078 | 11/1987 | Schirmer et al. | 560/60 |
| 4,723,034 | 2/1988 | Schirmer et al. | 560/60 |

FOREIGN PATENT DOCUMENTS 54-61159 5/1979 Japan ............... 560/15

OTHER PUBLICATIONS

Chem. Lett. (11), 1281-2 (1978) (Kaneko et al).
J. Org. Chem. 44 (16), 2916-20 (Krase et al) (1979).

Primary Examiner—Floyd D. Higel
Attorney, Agent, or Firm—Cushman, Darby & Cushman

[57] ABSTRACT

Compounds of formula:

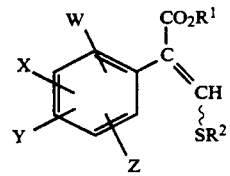

and stereoisomers thereof, wherein $R^1$ and $R^2$, which are the same or different, are optionally substituted alkyl; W, X, Y and Z, which are the same or different, are hydrogen, halogen, hydroxy, optionally substituted alkyl, optionally substituted cycloalkyl, optionally substituted cycloalkylalkyl, optionally substituted aralkyl, optionally substituted aryloxyalkyl, optionally substituted alkenyl, optionally substituted aryl, optionally substituted alkynyl, optionally substituted amino, optionally substituted arylazo, optionally substituted heteroarylalkyl, optionally substituted heteroaryloxyalkyl, optionally substituted acylamino, nitro, cyano, $-OR^3$, $-SR^3$, $-CO_2R^4$, $-CONR^5R^6$, $-COR^7$, $-CR^8=NR^9$, $-N=CR^{10}R^{11}$, $-SOR^{12}$ or $-SO_2R^{13}$, or any two of W, X, Y, and Z, in adjacent positions on the phenyl ring, optionally join to form an optionally substituted fused ring, either aromatic or aliphatic, optionally containing one or more heteroatoms; $R^3$ is optionally substituted alkyl, or cycloalkyl optionally containing a hetero atom in the cycloalkyl ring, optionally substituted alkenyl, optionally substituted aryl, optionally substituted aralkyl, optionally substituted acyl, or optionally substituted heteroaryl; $R^4$, $R^5$, $R^6$, $R^7$, $R^8$, $R^{10}$ and $R^{11}$, which are the same or different, are hydrogen or optionally substituted alkyl, optionally substituted cycloalkyl, cycloalkylalkyl, optionally substituted alkenyl, optionally substituted alkynyl, optionally substituted aryl, optionally substituted heteroaryl, or optionally substituted aralkyl; and $R^9$, $R^{12}$ and $R^{13}$ are optionally substituted aryl or optionally substituted heteroaryl. The compounds are useful in agriculture as fungicides, plant growth regulators and insecticides.

5 Claims, No Drawings

DERIVATIVES OF ALPHAPHENYLACRYLIC ACID AND THEIR USE IN AGRICULTURE

This invention relates to derivatives of acrylic acid useful in agriculture (especially as fungicides but also as plant growth regulators and insecticides), to processes for preparing them, to agricultural (especially fungicidal) compositions containing them, and to methods of using them to combat fungi (especially fungal infections in plants), to control or kill insect pests and to regulate plant growth.

The invention provides a compound having the formula (I):

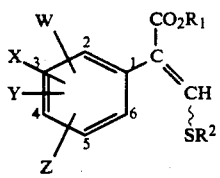 (I)

and stereoisomers thereof, wherein $R^1$ and $R^2$, which are the same or different, are optionally substituted alkyl (especially methyl); W, X, Y and Z, which are the same or different, are hydrogen, halogen (fluorine, chlorine, bromine or iodine), hydroxy, optionally substituted alkyl, optionally substituted cycloalkyl, optionally substituted cycloalkylalkyl, optionally substituted aralkyl, optionally substituted aryloxyalkyl, optionally substituted alkenyl, optionally substituted aryl, optionally substituted alkynyl, optionally substituted amino, optionally substituted arylazo, optionally substituted heteroarylalkyl, optionally substituted heteroaryloxyalkyl, optionally substituted acylamino, nitro, cyano, $-OR^3$, $-SR^3$, $-CO_2R^4$, $-CONR^5R^6$, $-COR^7$, $-CR^8=NR^9$, $-N=CR^{10}R^{11}$, $-SOR^{12}$ or $-SO_2R^{13}$, or any two of W, X, Y and Z in adjacent positions on the phenyl ring, optionally join to form an optionally substituted fused ring, either aromatic or aliphatic, optionally containing one or more heteroatoms; $R^3$ is optionally substituted alkyl or cycloalkyl optionally containing a hetero-atom in the cycloalkyl ring, optionally substituted alkenyl, optionally substituted aryl, optionally substituted aralkyl, optionally substituted acyl, or optionally substituted heteroaryl; $R^4$, $R^5$, $R^6$, $R^7$, $R^8$, $R^{10}$ and $R^{11}$, which are the same or different, are hydrogen or optionally substituted alkyl, optionally substituted cycloalkyl, optionally substituted cycloalkylalkyl, optionally substituted alkenyl, optionally substituted alkynyl, optionally substituted aryl, optionally substituted heteroaryl, or optionally substituted aralkyl; and $R^9$, $R^{12}$ and $R^{13}$ are optionally substituted aryl or optionally substituted heteroaryl.

The compounds of the invention contain at least one carbon-carbon double bond, and are sometimes obtained in the form of mixtures of geometric isomers. However, these mixtures can be separated into individual isomers, and this invention embraces such isomers, and mixtures thereof in all proportions including those which consist substantially of the (Z)-isomer and those which consist substantially of the (E)-isomer.

The individual isomers which result from the unsymmetrically substituted double bond of the acrylate group are identified by the commonly used terms "E" and "Z". These terms are defined according to the Cahn-Ingold-Prelog system which is fully described in the literature (see, for example, J March, "Advanced Organic Chemistry" 3rd edition, Wiley-Interscience, Page 109 et seq).

The use hereinafter of the formula:

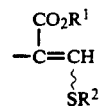

signifies a separable mixture of both geometric isomers about the acrylate double bond, ie

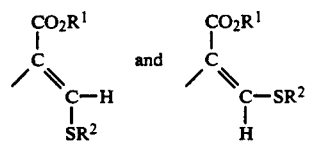

In the compounds of formula (I), alkyl groups and the alkyl moiety of alkoxy groups can be in the form of straight or branched chains and preferably contain 1 to 6 carbon atoms, more preferably 1 to 4 carbon atoms. Examples are methyl, ethyl, propyl (n- and iso-propyl) and butyl (n-, sec-, iso- and tert-butyl). Optional substituents of alkyl include hydroxy, halogen (especially chlorine or fluorine), and alkoxycarbonyl. Trifluoromethyl is an optionally substituted alkyl group of particular interest.

$R^1$ and $R^2$, which are optionally substituted alkyl groups, are preferably both methyl. When substituted, the preferred substituent is fluorine of which one or more atoms may be present.

Cycloalkyl, which is preferably $C_{3-6}$ cycloalkyl, includes cyclohexyl and cycloalkylalkyl, which is preferably $C_{3-6}$ cycloalkyl($C_{1-4}$)alkyl, includes cyclopropylethyl. An example of a cycloalkyl group containing a hetero-atom is tetrahydropyranyl.

Aralkyl includes, particularly, phenylalkyl (especially benzyl, phenylethyl, phenylpropyl, phenylbutyl or phenylhexyl) in which the alkyl moiety may carry other substituents such as hydroxy and the aryl moiety may be substituted with, for example, one or more of the following; halogen, hydroxy, $C_{1-4}$ alkyl (especially methyl and ethyl), $C_{1-4}$ alkoxy (especially methoxy), halo($C_{1-4}$) alkyl (especially trifluoromethyl), halo($C_{1-4}$)alkoxy (especially trifluoromethoxy), $C_{1-4}$ alkylthio (especially methylthio), $C_{1-4}$ alkoxy($C_{1-4}$)alkyl, $C_{3-6}$ cycloalkyl, $C_{3-6}$ cycloalkyl($C_{1-4}$)alkyl, aryl (especially phenyl), aryloxy (especially phenyloxy), aryl($C_{1-4}$)alkyl (especially benzyl, phenylethyl and phenyl n-propyl), aryl($C_{1-4}$)alkoxy (especially benzyloxy), aryloxy($C_{1-4}$)alkyl (especially phenyloxymethyl), carbacyl (especially acetyloxy and benzoyloxy), cyano, thiocyanato, nitro, $-NR'R''$, $-NHCOR'$, $-NHCONR'R''$, $-CONR'R''$, $-COOR''$, $-OSO_2R'$, $-SO_2R'$, $-COR'$, $-CR'=NR''$ or $-N=CR'R''$ in which $R'$ and $R''$ are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy.

Aryloxyalkyl includes, in particular, phenoxyalkyl (especially phenoxymethyl or phenoxyethyl) in which the alkyl moiety may carry other substituents such as hydroxy and the aryl moiety may be substituted in the same way as the aryl moiety in aralkyl above. Alkenyl and alkynyl groups preferably contain 2 to 6 carbon atoms and, more preferably, 2 to 4 carbon atoms in the form of straight or branched chains. Ethenyl, propenyl and butenyl are examples of alkenyl groups. Optional substituents of alkenyl (especially of ethenyl) include aromatic and heteroaromatic groups (such as phenyl, furyl, thienyl or pyridyl) which may themselves carry substituents such as those carried by the aryl moiety in aralkyl above, particularly halogen (especially chlorine or fluorine). Further, the terminal carbon atom of the alkenyl groups may form part of a 5- or 6-membered cycloalkyl group. Alkynyl includes ethenyl and is optionally substituted by, for example, aryl which may itself be substituted in the same way as the aryl moiety in aralkyl above.

Aryl is preferably phenyl; heteroaryl includes heteroaromatic groups such as pyridinyl, pyrimidinyl, pyrazinyl, pyridazinyl, 1,2,3-, 1,2,4-, and 1,3,5-triazinyl, 1,2,4,5-tetrazinyl, thienyl, quinolinyl, isoquinolinyl, quinoxalinyl and benzothiophenyl; either may be substituted in the same way as the aryl moiety in aralkyl above.

Optionally substituted amino, acylamino and acyl include the groups —NR'R", —NHCOR and —COR' in which R' and R" are as defined above. Acyl includes, in particular, formyl, acetyl and benzoyl, and acylamino includes benzoylamino and furoylamino optionally substituted by, for example, N-($C_{1-4}$)alkyl (especially N-methyl).

Arylazo is, for example, phenylazo in which the aryl moiety is optionally substituted in the same way as the aryl moiety in aralkyl above and particularly by alkynyl, alkoxy (especially methoxy) or dialkylamino (especially dimethylamino). Heteroarylalkyl and heteroaryloxyalkyl mean alkyl (preferably $C_{1-4}$ alkyl and especially ethyl in the case of heteroarylalkyl and methyl in the case of heteroaryloxyalkyl) carrying a heteroaromatic substituent (linked by an oxygen atom in the case of heteroaryloxyalkyl) which includes pyridinyl, pyrimidinyl, thienyl, furyl and pyrrolyl. The heteroaromatic moiety is optionally substituted in the same way as the aryl moiety in aralkyl above, and particularly by trifluoromethyl, halogen (especially fluorine, chlorine or bromine), nitro, $C_{1-4}$ alkyl, $C_{1-4}$ alkoxy, trifluoromethoxy and amino.

Whenever reference is made to an optionally substituted aryl or heteroaryl moiety, or optionally substituted fused ring, optional substituents include those which can be present in the aryl moiety of aralkyl as described above.

In one particular aspect, the invention provides compounds having the formula (Ia)

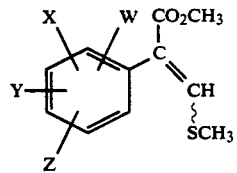

and stereoisomers thereof, wherein W, X, Y and Z, which are the same or different, are hydrogen, halogen (especially fluorine or chlorine), $C_{1-4}$ alkyl optionally substituted by hydroxy or $C_{1-4}$ alkoxycarbonyl, trifluoromethyl, phenyl($C_{1-4}$)alkyl, phenoxy($C_{1-4}$)alkyl, alkenyl (especially ethenyl, propenyl or butenyl) optionally substituted by an aromatic or heteroaromatic group (such as phenyl, furyl, thienyl or pyridinyl) which itself is optionally substituted with, for example, halogen (especially fluorine or chlorine) or in which the terminal carbon atom of the alkenyl group forms part of a 5- or 6-membered cycloalkyl group, optionally substituted $C_{2-4}$ alkynyl (for example, phenylethynyl), optionally substituted aryl (especially phenyl), amino substituted by aryl or $C_{1-4}$ alkyl groups (such as phenyl or methyl), arylazo (especially phenylazo) optionally substituted by, for example, $C_{1-4}$ alkyl, $C_{1-4}$ alkoxy (especially methoxy) or N,N-di($C_{1-4}$)alkylamino (especially N,N-dimethylamino) acylamino (especially benzoylamino or furoylamino) optionally substituted by, for example, N-alkyl (such as N-methyl), nitro, -$SR^3$ or -$OR^3$, in which $R^3$ is optionally substituted alkyl, optionally substituted aryl (especially phenyl), optionally substituted heteroaryl, optionally substituted aralkyl, or acyl (for example benzoyl), —$SOR^{12}$ or —$SO_2R^{13}$ in which $R^{12}$ and $R^{13}$ are aryl (for example phenyl), —$CO_2R^4$ in which $R^4$ is optionally substituted alkyl (especially $C_{1-4}$ alkyl, for example, tert-butyl), aryl (especially phenyl), $C_{3-6}$ cycloalkyl (especially cyclohexyl), $C_{3-6}$ cycloalkyl($C_{1-4}$)alkyl or aryl($C_{1-4}$)-alkyl, —$COR^7$ in which $R^7$ is optionally substituted alkyl (especially methyl) or optionally substituted aryl (for example phenyl or methoxyphenyl), or any two of W, X, Y and Z, in adjacent positions on the phenyl ring, join to form a fused ring (for example, a fused benzene, naphthalene or benzofuran ring).

It is preferred that at least one of W, X, Y and Z is other than hydrogen and that it is in a position on the phenyl ring ortho to the acrylate group.

It is further preferred that when more than one of W, X, Y and Z is other than hydrogen, the additional substituent or substituents are either single atoms or sterically small groups such as fluorine, chlorine, bromine, hydroxy, methyl, methoxy, methylthio, trifluoromethyl, trifluoromethoxy, nitro, cyano, amino, methylamino, dimethylamino, carboxy, acetyl and methoxycarbonyl.

In another aspect, the invention provides compounds having the formula (Ib):

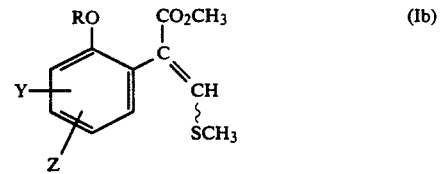

wherein R is hydrogen, $C_{1-4}$ alkyl optionally substituted by $C_{1-4}$ alkylthio, phenylthio or phenyl, $C_{3-6}$ cycloalkyl (especially cyclohexyl), tetrahydropyranyl, $C_{2-4}$ alkenyl (especially ethenyl, propenyl or phenylethenyl), phenyl optionally substituted by one or more of halogen (fluorine, chlorine, bromine or iodine), hydroxy, $C_{1-4}$ alkyl, $C_{1-4}$ alkoxy (especially methoxy), trifluoromethoxy, phenoxy, nitro, amino, aryl($C_{1-4}$)alkyl (especially benzyl), phenyl, carboxy, a carboxylic acid ester (especially the methyl ester), cyano, $C_{1-4}$ alkylcarbonylamino (especially methylcarbonylamino), or methylenedioxy, naphthyl, pyridinyl or pyrimidinyl, in which the pyridinyl and pyrimidinyl moieties are optionally substituted by halogen (especially fluorine, chlorine or bromine), trifluoromethyl, nitro, $C_{1-4}$ alkyl (especially methyl), $C_{1-4}$ alkoxy (especially methoxy), trifluoromethoxy or amino; and Y and Z, which are the same or different, are hydrogen, halogen (especially fluorine or chlorine), $C_{1-4}$ alkyl (especially methyl), $C_{1-4}$ alkoxy (especially methoxy), $C_{1-4}$ alkylthio (especially methylthio), trifluoromethyl, nitro, N,N-di($C_{1-4}$)alkylamino (specially N,N-dimethylamino), or Y and Z together form a methylenedioxy group.

In yet another aspect, the invention provides compounds having the formula (Ic):

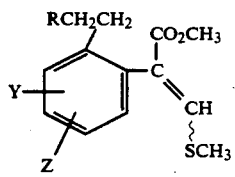  (Ic)

wherein R, Y and Z have the meanings given above in connection with the compounds of formula (Ib) except that, in addition, R may be thienyl, furyl or pyrrolyl.

In a still further aspect the invention provides compounds having the formula (Id):

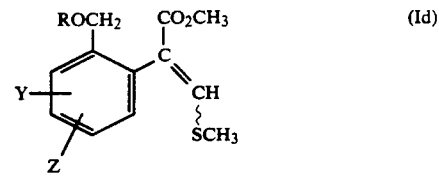  (Id)

wherein R, Y and Z have the meanings given above in connection with the compounds of formula (Ic).

The invention is illustrated by the compounds listed in Tables I and II which follow.

TABLE I

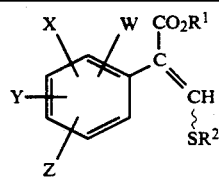  (I)

| Compound No. | $R^1$ | $R^2$ | X | Y | Z | Melting point (°C.) | olefinic* | isomer+ |
|---|---|---|---|---|---|---|---|---|
| 1 | $CH_3$ | $CH_3$ | H | H | H | 54–55 | 7.82 | E |
| 2 | $CH_3$ | $CH_3$ | H | H | H | oil | 7.09 | Z |
| 3 | $CH_3CH_2$ | $CH_3$ | H | H | H | | | E |
| 4 | $CH_3$ | $CH_3CH_2$ | H | H | H | | | E |
| 5 | $CH_3CH_2$ | $CH_3CH_2$ | H | H | H | | | E |
| 6 | $CH_3CH_2CH_2$ | $CH_3$ | H | H | H | | | E |
| 7 | $CH_3$ | $CH_3CH_2CH_2$ | H | H | H | | | E |
| 8 | $(CH_3)_3C$ | $CH_3$ | H | H | H | | | E |
| 9 | $CH_3$ | $CH_3$ | 2-(E—$C_6H_5$CH:CH) | H | H | oil | 7.94 | E |
| 10 | $CH_3$ | $CH_3$ | 2-(E—$C_6H_5$CH:CH) | H | H | oil | obscured by aromatic protons | Z |
| 11 | $CH_3$ | $CH_3$ | 3-(E—$C_6H_5$CH:CH) | H | H | | | E |
| 12 | $CH_3$ | $CH_3$ | 4-(E—$C_6H_5$CH:CH) | H | H | | | E |
| 13 | $CH_3$ | $CH_3$ | 2-(Z—$C_6H_5$CH:CH) | H | H | | | E |
| 14 | $CH_3$ | $CH_3$ | 2-(Z—$C_6H_5$CH:CH) | H | H | | | Z |
| 15 | $(CH_3)_3C$ | $CH_3$ | 2-(Z—$C_6H_5$CH:CH) | H | H | | | E |
| 16 | $CH_3$ | $(CH_3)_3C$ | 2-(Z—$C_6H_5$CH:CH) | H | H | | | E |
| 17 | $CH_3$ | $CH_3$ | 2-$C_6H_5CH_2CH(CH_3)$ | H | H | | | E |
| 18 | $CH_3$ | $CH_3$ | 2-$C_6H_5CH_2C(CH_3)_2$ | H | H | | | E |
| 19 | $CH_3$ | $CH_3$ | 2-$C_6H_5$C:C | H | H | | | E |
| 20 | $CH_3$ | $CH_3$ | 2-$CH_2$:CH | H | H | | | E |
| 21 | $CH_3$ | $CH_3$ | 2-Cl | H | H | | | E |
| 22 | $CH_3$ | $CH_3$ | 4-Cl | H | H | | | E |
| 23 | $CH_3$ | $CH_3$ | 2-Cl | 4-Cl | H | 108–110 | 7.45 | E |
| 24 | $CH_3$ | $CH_3$ | 2-Cl | 6-Cl | H | | | E |
| 25 | $CH_3$ | $CH_3$ | 3-Cl | 5-Cl | H | | | E |
| 26 | $CH_3$ | $CH_3$ | 3-Cl | 5-Cl | H | | | Z |
| 27 | $CH_3$ | $CH_3$ | 2-Cl | 6-F | H | | | E |
| 28 | $CH_3$ | $CH_3$ | 2-$CH_3$ | H | H | | | E |
| 29 | $CH_3$ | $CH_3$ | 2-$CH_3$ | H | H | | | Z |
| 30 | $CH_3$ | $CH_3$ | 2-($CO_2CH_3$) | H | H | | | E |
| 31 | $CH_3$ | $CH_3$ | 2-$CF_3$ | H | H | | | E |
| 32 | $CH_3$ | $CH_3$ | 2-$C_6H_5$ | H | H | | | E |
| 33 | $CH_3$ | $CH_3$ | 2-$C_6H_5N(CH_3)CO$ | H | H | | | E |
| 34 | $CH_3$ | $CH_3$ | 2-$C_6H_5CON(CH_3)$ | H | H | | | E |
| 35 | $CH_3$ | $CH_3$ | 2-$C_6H_5CO$ | H | H | | | E |
| 36 | $CH_3$ | $CH_3$ | 2-$C_6H_5CO_2$ | H | H | | | E |
| 37 | $CH_3$ | $CH_3$ | 2-$C_6H_5O_2C$ | H | H | | | E |
| 38 | $CH_3$ | $CH_3$ | 2-$(CH_3)_3CO_2C$ | H | H | | | E |
| 39 | $CH_3$ | $CH_3$ | 2-(cyclohexyl)$O_2C$ | H | H | | | E |
| 40 | $CH_3$ | $CH_3$ | 2-$C_6H_5CH_2$ | H | H | | | E |
| 41 | $CH_3$ | $CH_3$ | 2-(4-Cl—$C_6H_4$)$CH_2$ | H | H | | | E |
| 42 | $CH_3$ | $CH_3$ | 2-(4-$CH_3O$—$C_6H_4$)$CH_2$ | H | H | | | E |
| 43 | $CH_3$ | $CH_3$ | 2-$C_6H_5(CH_3)_2C$ | H | H | | | E |
| 44 | $CH_3$ | $CH_3$ | 2-$C_6H_5CH(OH)$ | H | H | | | E |
| 45 | $CH_3$ | $CH_3$ | 2-$NO_2$ | H | H | | | E |
| 46 | $CH_3$ | $CH_3$ | 2-$NH_2$ | H | H | | | E |

TABLE I-continued

| | | | | | | | |
|---|---|---|---|---|---|---|---|
| 47 | CH₃ | CH₃ | 2-C₆H₅N:N | H | H | | E |
| 48 | CH₃ | CH₃ | 2-(4-(CH₃)₂N—C₆H₄N:N) | H | H | | E |
| 49 | CH₃ | CH₃ | 2-(4-CH₃O—C₆H₄N:N) | H | H | | E |
| 50 | CH₃ | CH₃ | 2-CH₃O₂CCH₂CH₂ | H | H | | E |
| 51 | CH₃ | CH₃ | 2-(CH₃)₂CH | H | H | | E |
| 52 | CH₃ | CH₃ | 2-C₆H₅S | H | H | | E |
| 53 | CH₃ | CH₃ | 2-C₆H₅S(O) | H | H | | E |
| 54 | CH₃ | CH₃ | 2-C₆H₅S(O)₂ | H | H | | E |
| 55 | CH₃ | CH₃ | 2-(E— 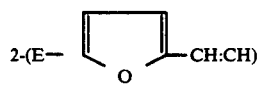 —CH:CH) | H | H | | E |
| 56 | CH₃ | CH₃ | 2-(E— 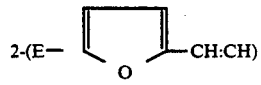 —CH:CH) | H | H | | Z |
| 57 | CH₃ | CH₃ | 2-(4-Cl—C₆H₄OCH₂) | H | H | | E |
| 58 | CH₃ | CH₃ | 2-(3-CH₃CH₃O—C₆H₄OCH₂) | H | H | | E |
| 59 | CH₃ | CH₃ | 2-(3-CH₃—C₆H₄OCH₂) | H | H | | E |
| 60 | CH₃ | CH₃ | ⊕ | ⊕ | H | | E |
| 61 | CH₃ | CH₃ | ⊕ | ⊕ | H | | E |
| 62 | CH₃ | CH₃ | ⊕ | ⊕ | H | | E |
| 63 | CH₃ | CH₃ | ⊕ | ⊕ | ⊕° | | E |
| 64 | CH₃ | CH₃ | ⊕ | ⊕ | H | | E |
| 65 | CH₃ | CH₃ | ⊕ | ⊕ | H | | E |
| 66 | CH₃ | CH₃ | ⊕ | ⊕ | H | | E |
| 67 | CH₃ | CH₃ | ⊕ | ⊕ | H | | E |
| 68 | CH₃ | CH₃ | ⊕ | ⊕ | H | | E |
| 69 | CH₃ | CH₃ | 2-(C₆H₅N(CH₃)) | H | H | | E |
| 70 | CH₃ | CH₃ | 2-(4-CH₃O—C₆H₄CO) | H | H | | E |
| 71 | CH₃ | CH₃ | 2-C₆H₅OCH₂ | H | H | | E |
| 72 | CH₃ | CH₃ | 2-C₆H₅CH(CH₃)CH₂ | H | H | | E |
| 73 | CH₃ | CH₃ | 2-C₆H₅C(CH₃)₂CH₂ | H | H | | E |
| 74 | CH₃ | CH₃ | 2-( 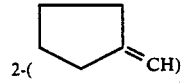 CH) | H | H | | E |
| 75 | CH₃ | CH₃ | 2-(E-4-Cl—C₆H₄CH:CH) | H | H | | E |
| 76 | CH₃ | CH₃ | 2-(E-4-F—C₆H₄CH:CH) | H | H | | E |
| 77 | CH₃ | CH₃ | 2-(E-2,6-di-Cl—C₆H₃CH:CH) | H | H | | E |
| 78 | CH₃ | CH₃ | 2-(E-C₆H₅C(CH₃):C(CH₃)) | H | H | | E |
| 79 | CH₃ | CH₃ | 2-(E-C₆H₅C(CH₃):CH) | H | H | | E |
| 80 | CH₃ | CH₃ | 2-(E-C₆H₅CH:C(CH₃)) | H | H | | E |
| 81 | CH₃ | CH₃ | 2-(E— 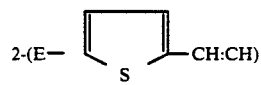 —CH:CH) | H | H | | E |
| 82 | CH₃ | CH₃ | 2-(E— 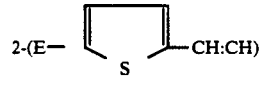 —CH:CH) | H | H | | Z |
| 83 | CH₃ | CH₃ | 2-C₆H₅OCH₂ | H | H | | Z |
| 84 | CH₃ | CH₃ | 2-C₆H₅OCH(CH₃) | H | H | | E |
| 85 | CH₃ | CH₃ | 2-C₆H₅OC(CH₃)₂ | H | H | | E |
| 86 | CH₃ | CH₃ | 2-C₆H₅C(CH₃)₂C(CH₃)₂ | H | H | | E |
| 87 | CH₃ | CH₃ | 2-(E— 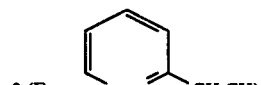 —CH:CH) | H | H | | E |
| 88 | CH₃ | CH₃ | 2-(E— 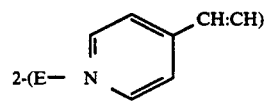 —CH:CH) | H | H | | E |
| 89 | CH₃ | CH₃ | 2-(E— 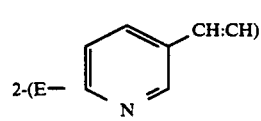 —CH:CH) | H | H | | E |

TABLE I-continued

| | | | | | | | | |
|---|---|---|---|---|---|---|---|---|
| 90 | CH₃ | CH₃ | 2(C₆H₅)₂C:OH | H | H | | | E |
| 91 | CH₃ | CH₃ | 2-(cyclohexyl=CH) | H | H | | | E |
| 92 | CH₃ | CH₃ | 2-C₆H₅CONH | H | H | | | E |
| 93 | CH₃ | CH₃ | 2-C₆H₅NHCO | H | H | | | E |
| 94 | CH₃ | CH₃ | 2-(furyl-CONH) | H | H | | | E |
| 95 | CH₃ | CH₃ | 2-(CH₃CH₂CH₂O₂C) | H | H | | | E |
| 96 | CH₃ | CH₃ | 2-(4-F—C₆H₄CH₂CH₂) | H | H | oil | 7.90 | E |
| 97 | CH₃ | CH₃ | 2-(2-furylCH₂CH₂) | H | H | oil | 7.99 | E |

NB
Throughout this table W is H except in compound 63 where it forms a fused benzene ring with Z.
Substituents are fused rings (see below)
*Here Z forms a fused benzene ring with W Thus compound 60 is:

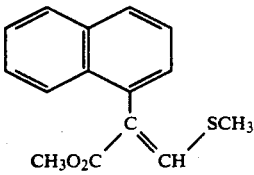

Compound 61 is:

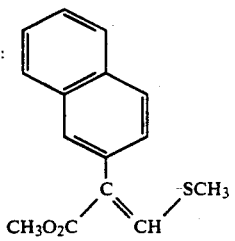

Compound 62 is:

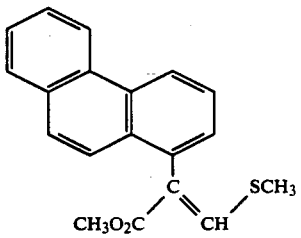

Compound 63 is:

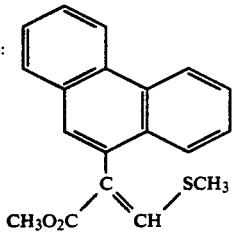

Compound 64 is:

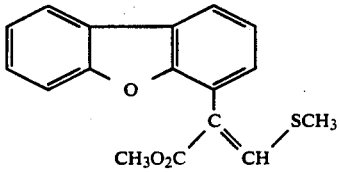

TABLE I-continued

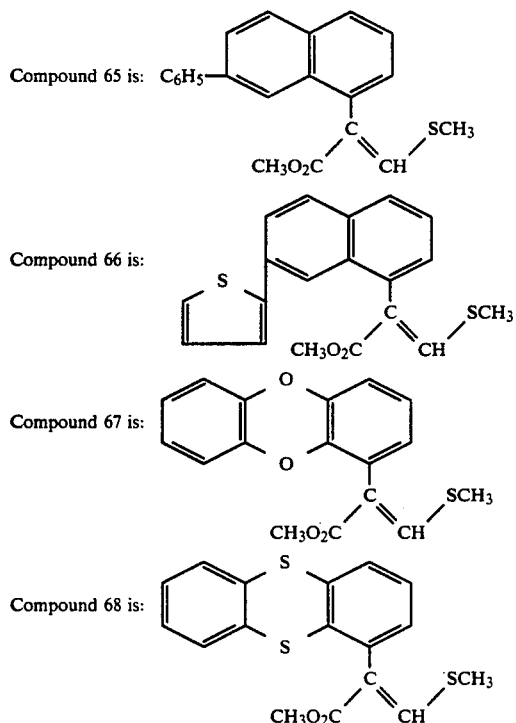

Compound 65 is:
Compound 66 is:
Compound 67 is:
Compound 68 is:

*Chemical shift of singlet from olefinic proton on beta-(alkylthio)acrylate group (ppm from tetramethylsilane). Solvent: $CDCl_3$
+Geometry of the beta-(alkylthio)acrylate group.

TABLE II

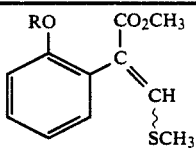

| Compound No. | R | Melting point (°C.) | olefinic* | isomer+ |
|---|---|---|---|---|
| 1 | $C_6H_5$ | 98–98.5 | 7.77 | E |
| 2 | 2-F—$C_6H_4$ | | | E |
| 3 | 3-F—$C_6H_4$ | | | E |
| 4 | 4-F—$C_6H_4$ | | | E |
| 5 | 2-Cl—$C_6H_4$ | | | E |
| 6 | 3-Cl—$C_6H_4$ | | | E |
| 7 | 4-Cl—$C_6H_4$ | | | E |
| 8 | 2-Br—$C_6H_4$ | | | E |
| 9 | 3-Br—$C_6H_4$ | | | E |
| 10 | 4-Br—$C_6H_4$ | | | E |
| 11 | 2-I—$C_6H_4$ | | | E |
| 12 | 3-I—$C_6H_4$ | | | E |
| 13 | 4-I—$C_6H_4$ | | | E |
| 14 | 2-$CH_3$—$C_6H_4$ | | | E |
| 15 | 3-$CH_3$—$C_6H_4$ | | | E |
| 16 | 4-$CH_3$—$C_6H_4$ | | | E |
| 17 | 2-$CH_3CH_2$—$C_6H_4$ | | | E |
| 18 | 3-$CH_3CH_2$—$C_6H_4$ | | | E |
| 19 | 4-$CH_3CH_2$—$C_6H_4$ | | | E |
| 20 | 2-$(CH_3)_2CH$—$C_6H_4$ | | | E |
| 21 | 3-$(CH_3)_2CH$—$C_6H_4$ | | | E |
| 22 | 4-$(CH_3)_2CH$—$C_6H_4$ | | | E |
| 23 | 2-$(CH_3)_3C$—$C_6H_4$ | | | E |
| 24 | 3-$(CH_3)_3C$—$C_6H_4$ | | | E |
| 25 | 4-$(CH_3)_3C$—$C_6H_4$ | | | E |
| 26 | 2-$CH_3O$—$C_6H_4$ | | | E |
| 27 | 3-$CH_3O$—$C_6H_4$ | | | E |
| 28 | 4-$CH_3O$—$C_6H_4$ | | | E |
| 29 | 2-$CF_3O$—$C_6H_4$ | | | E |
| 30 | 3-$CF_3O$—$C_6H_4$ | | | E |
| 31 | 4-$CF_3O$—$C_6H_4$ | | | E |
| 32 | 2-$C_6H_5O$—$C_6H_4$ | | | E |

TABLE II-continued

[Structure: benzene ring with RO substituent and C(CO₂CH₃)=CH-SCH₃ group]

| Compound No. | R | Melting point (°C.) | olefinic* | isomer+ |
|---|---|---|---|---|
| 33 | 3-C₆H₅O—C₆H₄ | | | E |
| 34 | 4-C₆H₅O—C₆H₄ | | | E |
| 35 | 2-NO₂—C₆H₄ | | | E |
| 36 | 3-NO₂—C₆H₄ | | | E |
| 37 | 4-NO₂—C₆H₄ | | | E |
| 38 | 2-NH₂—C₆H₄ | | | E |
| 39 | 3-NH₂—C₆H₄ | | | E |
| 40 | 4-NH₂—C₆H₄ | | | E |
| 41 | 2-C₆H₅—C₆H₄ | | | E |
| 42 | 3-C₆H₅—C₆H₄ | | | E |
| 43 | 4-C₆H₅—C₆H₄ | | | E |
| 44 | 2-HO₂C—C₆H₄ | | | E |
| 45 | 3-HO₂C—C₆H₄ | | | E |
| 46 | 4-HO₂C—C₆H₄ | | | E |
| 47 | 2-CH₃O₂C—C₆H₄ | | | E |
| 48 | 3-CH₃O₂C—C₆H₄ | | | E |
| 49 | 4-CH₃O₂C—C₆H₄ | | | E |
| 50 | 2-(CN)—C₆H₄ | | | E |
| 51 | 3-(CN)—C₆H₄ | | | E |
| 52 | 4-(CN)—C₆H₄ | | | E |
| 53 | 2-HO—C₆H₄ | | | E |
| 54 | 3-HO—C₆H₄ | | | E |
| 55 | 4-HO—C₆H₄ | | | E |
| 56 | 2-CH₃C(O)NH—C₆H₄ | | | E |
| 57 | 3-CH₃C(O)NH—C₆H₄ | | | E |
| 58 | 4-CH₃C(O)NH—C₆H₄ | | | E |
| 59 | 2,3-di-F—C₆H₃ | | | E |
| 60 | 2,4-di-F—C₆H₃ | | | E |
| 61 | 2,5-di-F—C₆H₃ | | | E |
| 62 | 2,6-di-F—C₆H₃ | | | E |
| 63 | 3,4-di-F—C₆H₃ | | | E |
| 64 | 3,5-di-F—C₆H₃ | | | E |
| 65 | 2,3-di-Cl—C₆H₃ | | | E |
| 66 | 2,4-di-Cl—C₆H₃ | | | E |
| 67 | 2,5-di-Cl—C₆H₃ | | | E |
| 68 | 3,4-di-Cl—C₆H₃ | | | E |
| 69 | 3,5-di-Cl—C₆H₃ | | | E |
| 70 | 2,3-di-CH₃—C₆H₃ | | | E |
| 71 | 2,4-di-CH₃—C₆H₃ | | | E |
| 72 | 2,5-di-CH₃—C₆H₃ | | | E |
| 73 | 3,4-di-CH₃—C₆H₃ | | | E |
| 74 | 3,5-di-CH₃—C₆H₃ | | | E |
| 75 | 2,3-di-CH₃O—C₆H₃ | | | E |
| 76 | 2,4-di-CH₃O—C₆H₃ | | | E |
| 77 | 2,5-di-CH₃O—C₆H₃ | | | E |
| 78 | 3,4-di-CH₃O—C₆H₃ | | | E |
| 79 | 3,5-di-CH₃O—C₆H₃ | | | E |
| 80 | 2-F,3-Cl—C₆H₃ | | | E |
| 81 | 2-F,4-Cl—C₆H₃ | | | E |
| 82 | 2-F,5-Cl—C₆H₃ | | | E |
| 83 | 2-F,6-Cl—C₆H₃ | | | E |
| 84 | 3-F,4-Cl—C₆H₃ | | | E |
| 85 | 3-F,5-Cl—C₆H₃ | | | E |
| 86 | 2-Cl-3-F—C₆H₃ | | | E |
| 87 | 2-Cl,4-F—C₆H₃ | | | E |
| 88 | 2-Cl,5-F—C₆H₃ | | | E |
| 89 | 3-Cl,4-F—C₆H₃ | | | E |
| 90 | 2-F,3-CH₃—C₆H₃ | | | E |
| 91 | 2-F,4-CH₃—C₆H₃ | | | E |
| 92 | 2-F,5-CH₃—C₆H₃ | | | E |
| 93 | 2-F,6-CH₃—C₆H₃ | | | E |
| 94 | 3-F,4-CH₃—C₆H₃ | | | E |
| 95 | 3-F,5-CH₃—C₆H₃ | | | E |
| 96 | 2-CH₃,3-F—C₆H₃ | | | E |
| 97 | 2-CH₃,4-F—C₆H₃ | | | E |
| 98 | 2-CH₃,5-F—C₆H₃ | | | E |
| 99 | 3-CH₃,4-F—C₆H₃ | | | E |
| 100 | 2-F,3-CH₃O—C₆H₃ | | | E |
| 101 | 2-F,4-CH₃O—C₆H₃ | | | E |
| 102 | 2-F,5-CH₃O—C₆H₃ | | | E |
| 103 | 2-F,6-CH₃O—C₆H₃ | | | E |
| 104 | 3-F,4-CH₃O—C₆H₃ | | | E |

TABLE II-continued

Structure: phenyl ring with OR substituent (ortho), and C(CO₂CH₃)=CH-SCH₃ group

| Compound No. | R | Melting point (°C.) | olefinic* | isomer+ |
|---|---|---|---|---|
| 105 | 3-F,5-CH₃O—C₆H₃ | | | E |
| 106 | 2-CH₃O,3-F—C₆H₃ | | | E |
| 107 | 2-CH₃O,4-F—C₆H₃ | | | E |
| 108 | 2-CH₃O,5-F—C₆H₃ | | | E |
| 109 | 3-CH₃O,4-F—C₆H₃ | | | E |
| 110 | 2-Cl,3-CH₃—C₆H₃ | | | E |
| 111 | 2-Cl,4-CH₃—C₆H₃ | | | E |
| 112 | 2-Cl,5-CH₃—C₆H₃ | | | E |
| 113 | 3-Cl,4-CH₃—C₆H₃ | | | E |
| 114 | 3-Cl,5-CH₃—C₆H₃ | | | E |
| 115 | 2-CH₃,3-Cl—C₆H₃ | | | E |
| 116 | 2-CH₃,4-Cl—C₆H₃ | | | E |
| 117 | 2-CH₃,5-Cl—C₆H₃ | | | E |
| 118 | 3-CH₃,4-Cl—C₆H₃ | | | E |
| 119 | 2-Cl,3-CH₃O—C₆H₃ | | | E |
| 120 | 2-Cl,4-CH₃O—C₆H₃ | | | E |
| 121 | 2-Cl,5-CH₃O—C₆H₃ | | | E |
| 122 | 3-Cl,4-CH₃O—C₆H₃ | | | E |
| 123 | 3-Cl,5-CH₃O—C₆H₃ | | | E |
| 124 | 2-CH₃O,3-Cl—C₆H₃ | | | E |
| 125 | 2-CH₃O,4-Cl—C₆H₃ | | | E |
| 126 | 2-CH₃O,5-Cl—C₆H₃ | | | E |
| 127 | 3-CH₃O,4-Cl—C₆H₃ | | | E |
| 128 | 2-CH₃,3-CH₃O—C₆H₃ | | | E |
| 129 | 2-CH₃,4-CH₃O—C₆H₃ | | | E |
| 130 | 2-CH₃,5-CH₃O—C₆H₃ | | | E |
| 131 | 3-CH₃,4-CH₃O—C₆H₃ | | | E |
| 132 | 3-CH₃,5-CH₃O—C₆H₃ | | | E |
| 133 | 2-CH₃O,3-CH₃—C₆H₃ | | | E |
| 134 | 2-CH₃O,4-CH₃—C₆H₃ | | | E |
| 135 | 2-CH₃O,5-CH₃—C₆H₃ | | | E |
| 136 | 3-CH₃O,4-CH₃—C₆H₃ | | | E |
| 137 | 2,4,6-tri-F—C₆H₂ | | | E |
| 138 | 2,6-di-F,4-Cl—C₆H₂ | | | E |
| 139 | Pentafluorophenyl | | | E |
| 140 | H | | | E |
| 141 | CH₃ | | | E |
| 142 | CH₃CH₂ | | | E |
| 143 | CH₃CH₂CH₂ | | | E |
| 144 | (CH₃)₂CH | | | E |
| 145 | CH₃CH₂CH₂CH₂ | | | E |
| 146 | (CH₃)₃C | | | E |
| 147 | Cyclohexyl | | | E |
| 148 | CH₂:CHCH₂ | | | E |
| 149 | E-C₆H₅CH:CHCH₂ | | | E |
| 150 | CH₂:C(CH₃)CH₂ | | | E |
| 151 | E-CH₃CH:CHCH₂ | | | E |
| 152 | 2-tetrahydropyranyl | | | E |
| 153 | 3,4-methylenedioxyphenyl | | | E |
| 154 | CH₃SCH₂ | | | E |
| 155 | C₆H₅SCH₂ | | | E |
| 156 | C₆H₅CH₂ | | | E |
| 157 | C₆H₅C(CH₃)₂ | | | E |
| 158 | 4-Cl—C₆H₄C(CH₃)₂ | | | E |
| 159 | CH₃ | | | Z |
| 160 | C₆H₅ | | | Z |
| 161 | Pyridin-2-yl | | | E |
| 162 | Pyridin-3-yl | | | E |
| 163 | Pyridin-4-yl | | | E |
| 164 | 5-(trifluoromethyl)-pyridin-2-yl | | | E |
| 165 | Pyrimidin-2-yl | | | E |
| 166 | Pyrimidin-4-yl | | | E |
| 167 | Pyrimidin-5-yl | | | E |
| 168 | 3-Fluoropyridin-2-yl | | | E |
| 169 | 3-Chloropyridin-2-yl | | | E |
| 170 | 4-Bromopyridin-2-yl | | | E |
| 171 | 5-Methylpyridin-2-yl | | | E |
| 172 | 6-methoxypyridin-2-yl | | | E |
| 173 | 2-Fluoropyridin-3-yl | | | E |
| 174 | 4-(Trifluoromethyl)pyridin-3-yl | | | E |
| 175 | 5-Methylpyridin-3-yl | | | E |

TABLE II-continued

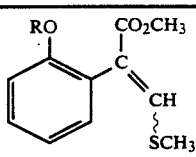

| Compound No. | R | Melting point (°C.) | olefinic* | isomer+ |
|---|---|---|---|---|
| 176 | 6-Methoxypyridin-3-yl | | | E |
| 177 | 2-Chloropyridin-4-yl | | | E |
| 178 | 3-(Trifluoromethyl)pyridin-4-yl | | | E |
| 179 | 4-Fluoropyrimidin-2-yl | | | E |
| 180 | 5-Methylpyrimidin-2-yl | | | E |
| 181 | 2-Chloropyrimidin-4-yl | | | E |
| 182 | 5-Methoxypyrimidin-4-yl | | | E |
| 183 | 6-(Trifluoromethyl)pyrimidin-4-yl | | | E |
| 184 | 2-Bromopyrimidin-5-yl | | | E |
| 185 | 4-Methylpyrimidin-5-yl | | | E |
| 186 | 3-Fluoro-5-(trifluoromethyl)-pyridin-2-yl | | | E |
| 187 | 3,6-Dichloro-5-(trifluoromethyl)-pyridin-2-yl | | | E |
| 188 | 6-Chloro-4-cyanopyridin-2-yl | | | E |
| 189 | 3-Cyano-5-nitropyridin-2-yl | | | E |
| 190 | 2-Chloro-6-fluoropyridin-4-yl | | | E |
| 191 | 4,6-Difluoropyridin-2-yl | | | E |
| 192 | 3,5-Dichloro-6-fluoropyridin-2-yl | | | E |
| 193 | 6-Methoxy-3-nitropyridin-2-yl | | | E |
| 194 | 4-Cyano-6-fluoropyridin-2-yl | | | E |
| 195 | 4-Cyano-3,5,6-trifluoropyridin-2-yl | | | E |
| 196 | 4-Cyano-2,5,6-trifluoropyridin-3-yl | | | E |
| 197 | 6-Chloro-5-nitropyridin-2-yl | | | E |
| 198 | 4,6-Dicynaopyridin-2-yl | | | E |
| 199 | 5-(Trichloromethyl)pyridin-2-yl | | | E |
| 200 | 5-Cyanopyridin-2-yl | | | E |
| 201 | 5-Bromo-4-(trifluoromethyl)pyridin-2-yl | | | E |
| 202 | 3-Nitro-5-(trifluoromethyl)pyridin-2-yl | | | E |
| 203 | 5-Formamidopyridin-2-yl | | | E |
| 204 | 5-Aminopyridin-2-yl | | | E |
| 205 | 2,3,5,6-Tetrafluoropyridin-4-yl | | | E |
| 206 | 5-Nitropyridin-2-yl | | | E |
| 207 | 4-Methyl-5-nitropyridin-2-yl | | | E |
| 208 | 5-(Difluoromethyl)pyridin-2-yl | | | E |
| 209 | 5-(Fluoromethyl)pyridin-2-yl | | | E |
| 210 | 4,6-Difluoropyrimidin-2-yl | | | E |
| 211 | 2-Chloro-6-(trichlormethyl)pyrimidin-4-yl | | | E |
| 212 | 2,6-Dichloropyrimidin-4-yl | | | E |
| 213 | 5-(Methoxycarbonyl)pyridin-2-yl | | | E |
| 214 | 5-Chloro-6-methoxypyridin-2-yl | | | E |
| 215 | 5,6-Dichloropyridin-2-yl | | | E |
| 216 | 6-Bromo-5-chloropyridin-2-yl | | | E |
| 217 | 5-Chloro-6-acetoxypyridin-2-yl | | | E |
| 218 | 5-Bromo-6-fluoropyridin-2-yl | | | E |
| 219 | 5-Bromo-6-cyanopyridin-2-yl | | | E |
| 220 | 5-Bromo-6-hydroxypyridin-2-yl | | | E |
| 221 | 5-Bromo-6-methoxypyridin-2-yl | | | E |
| 222 | 5,6-Dibromopyridin-2-yl | | | E |
| 223 | 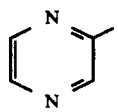 | | | |
| 224 | 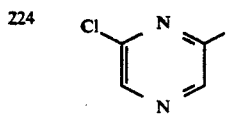 | | | |

TABLE II-continued

[Structure: RO-phenyl-C(=CH-SCH₃)(CO₂CH₃)]

| Compound No. | R | Melting point (°C.) | olefinic* | isomer+ |
|---|---|---|---|---|
| 225 | 2,5-dimethylpyrazin-3-yl | | | |
| 226 | pyridazin-3-yl (methyl) | | | |
| 227 | 6-chloro-pyridazin-3-yl (methyl) | | | |
| 228 | 1,2,3-triazin-4-yl (methyl) | | | |
| 229 | 1,2,3-triazin-5-yl (methyl) | | | |
| 230 | 1,2,4-triazin-6-yl (methyl) | | | |
| 231 | 1,3,5-triazin-2-yl (methyl) | | | E |
| 232 | 1,2,4,5-tetrazin-3-yl (methyl) | | | E |
| 233 | thien-2-yl | | | E |
| 234 | thien-2-yl | | | E |
| 235 | 3-chloro-4-methyl-thien-2-yl | | | E |
| 236 | 2-chloro-thien-3-yl | | | E |

TABLE II-continued

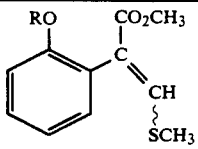

| Compound No. | R | Melting point (°C.) | olefinic* | isomer+ |
|---|---|---|---|---|
| 237 | 5-chloro-thiophen-3-yl | | | E |
| 238 | 4-chloro-thiophen-2-yl | | | E |
| 239 | 5-chloro-thiophen-2-yl | | | E |
| 240 | Naphth-1-yl | | | E |
| 241 | Naphth-2-yl | | | E |
| 242 | quinolin-6-yl | | | E |
| 243 | quinolin-2-yl | | | E |
| 244 | isoquinolin-6-yl | | | E |
| 245 | quinoxalin-6-yl | | | E |
| 246 | quinoxalin-2-yl | | | E |
| 247 | benzothiophen-2-yl | | | E |
| 248 | benzothiophen-5-yl | | | E |
| 249 | 5-fluoropyridin-2-yl | | | E |
| 250 | 5-chloropyridin-2-yl | | | E |
| 251 | 5-nitropyridin-2-yl | | | E |
| 252 | 5-methoxypyridin-2-yl | | | E |
| 253 | 5-(trifluormethoxy)pyridin-2-yl | | | E |

*chemical shift of singlet from olefinic proton on beta-(methylthio)acrylate group (ppm from tetramethylsilane).
+Geometry of beta-(methylthio)acrylate group.

The invention is also illustrated by the compounds of the formula:

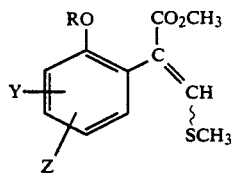

in which R has any of the values of R given in Table II and Y and Z are single atoms or sterically small groups such as hydrogen (provided both are not hydrogen), fluorine, chlorine, bromine, hydroxy, methyl, methoxy, methylthio, trifluoromethyl, trifluoromethoxy, nitro, cyano, amino, methylamino, dimethylamino, carboxy, acetyl and methoxycarbonyl, Examples of substitution patterns are given below in Table III. The acrylate group may have either the (E)- or the (Z)-geometry in each case.

TABLE III

| Y | Z |
|---|---|
| 3-F | H |
| 4-F | H |
| 5-F | H |
| 6-F | H |
| 3-Cl | H |
| 4-Cl | H |
| 5-Cl | H |
| 6-Cl | H |
| 3-$CH_3$ | H |
| 4-$CH_3$ | H |
| 5-$CH_3$ | H |
| 6-$CH_3$ | H |
| 3-$NO_2$ | H |
| 4-$NO_2$ | H |
| 5-$NO_2$ | H |
| 6-$NO_2$ | H |
| 5-$CF_3$ | H |
| 3-$NO_2$ | 5-Cl |
| 3-$NO_2$ | 5-$NO_2$ |
| 5-$CH_3S$ | H |
| 4-$CH_3O$ | 5-$CH_3O$ |
| 4-$(CH_3)_2N$ | H |
| 4,5-methylenedioxy | |

Specific examples of compounds of the type shown in Table III are as follows:

| Compound No.* | R | Y | Z | Melting Point (°C.) | Olefinic* | Isomer+ |
|---|---|---|---|---|---|---|
| 1 | $C_6H_5$ | 3-Cl | H | | | E |
| 2 | $C_6H_5$ | 4-$NO_2$ | H | | | E |
| 3 | $C_6H_5$ | 5-Cl | H | | | E |
| 4 | $C_6H_5$ | 6-$NO_2$ | H | | | E |
| 5 | $C_6H_5$ | 5-$NO_2$ | H | | | E |

*Chemical shift of singlet from olefinic proton on beta-(methylthio)acrylate group (ppm from tetramethylsilane). Solvent $CDCl_3$
+Geometry of beta-(methylthio)acrylate group.

The invention is further illustrated by the compounds of the formula

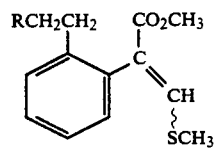

in which R has any of the values given for R in Table II. These compounds include compounds 50, 96 and 97 of Table I.

The invention is still further illustrated by the compounds of the formula

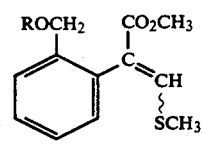

in which R has any of the values given for R in Table II. These compounds include compounds 57-59, 71 and 83 of Table I.

The invention is yet further illustrated by the compounds in which the moieties

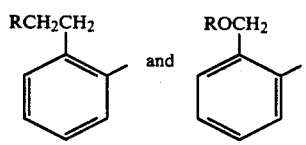

carry substituents Y and Z which have the same meanings as defined above in connection with the compounds of Table II, including the combinations of meanings as defined in Table III.

TABLE IV

SELECTED PROTON NMR DATA
Table IV shows selected proton NMR data for certain compounds described in Table I. Chemical shifts are measured in ppm from tetramethylsilane, and deuterochloroform was used as solvent throughtout. The following abbreviations are used:

| ppm = parts per million | NMR = nuclear magnetic resonance |
|---|---|
| br = broad | t = triplet |
| s = singlet | q = quartet |
| d = doublet | m = multiplet |
| J = coupling constant | Hz = Hertz |

| TABLE NO. | COMPOUND NO. | |
|---|---|---|
| I | 2 | 2.43(3H, s), 3.79(3H, s), 7.09 (1H, s). |
| I | 9 | 2.36(3H, s), 3.67(3H, s), 7.00 and 7.09(each 1H, d J 16Hz), 7.94(1H, s). |
| I | 10 | 2.40(3H, s), 3.69(3H, s), 7.04 (2H, looks like br s), olefinic singlet obscured by aromatic protons |

The compounds of the invention having the formula (I) can be prepared from a variety of intermediates as shown in Scheme I. The compounds exist as geometric isomers which can be separated by chromatography, distillation or fractional crystallisation. Throughout Scheme I the terms W, X, Y, Z, $R^1$ and $R^2$ are as defined above, $R^{14}$ is an alkyl group, and $R^{15}$ is an alkyl or an optionally substituted aryl group.

Scheme I

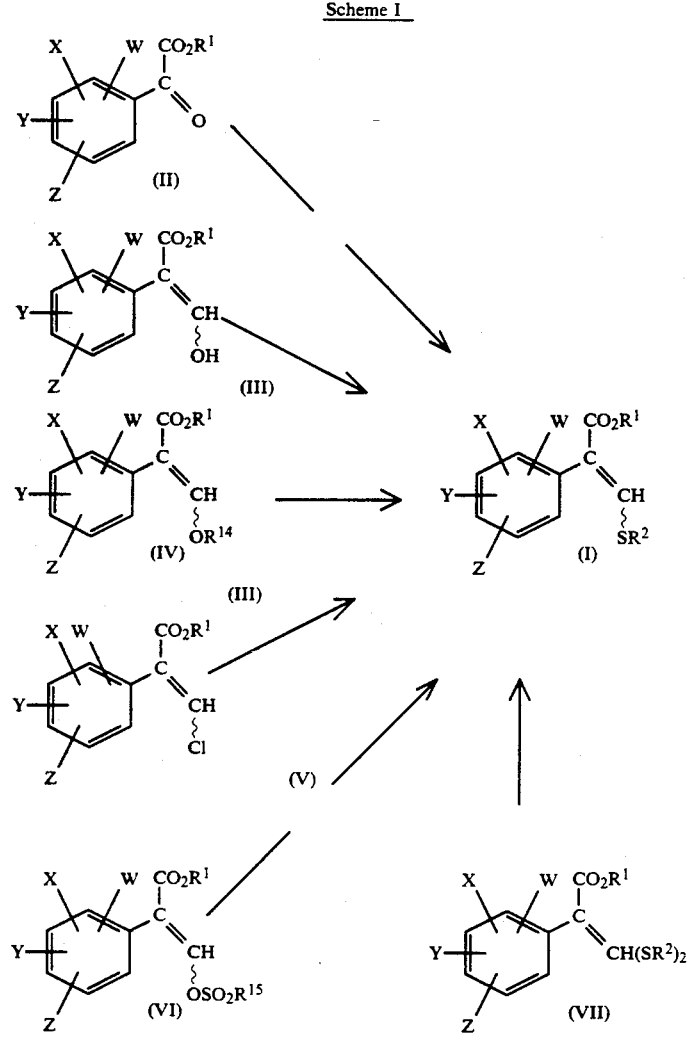

Thus compounds of the invention having the formula (I) can be prepared by the following methods. Each transformation is often performed in a convenient solvent.

(i) From alpha-ketoesters of formula (II) by treatment with phosphoranes of formula $Ph_3P^+\text{-}^-CHSR^2$, or with lithio-species of formula $Me_3SiCH(Li)SR^2$ (see, for example, D J Peterson *J.Org.Chem.*, 1968, 33, 780; F A Carey and A S Court, *J.Org.Chem.*, 1972, 37, 939).

(ii) From enols of formula (III; these compounds are in equilibrium with the tautomeric formylacetates) by treatment with thiols of formula $R^2SH$ under acidic conditions, often in the presence of a dehydrating agent (see, for example, P R Bernstein, *Tetrahedron Letters*, 1979, 1015).

(iii) From beta-alkoxyacrylates of formula (IV) by treatment with thiols of formula $R^2SH$ under acidic conditions, or by treatment with thiolates of formula $R^2SM$, wherein M is a metal ion, such as a sodium ion.

(iv) From beta-chloroacrylates of formula (V) by treatment with thiolates of formula $R^2SM$, wherein M is a metal ion, such as a sodium ion.

(v) From beta-sulphonyloxyacrylates of formula (VI) by treatment with thiolates of formula $R^2SM$, wherein M is a metal ion, such as sodium ion.

(vi) From dithio-acetals of formula (VII) by elimination of the elements of thiols of formula $R^2SH$ under acidic or basic conditions.

The intermediates shown in Scheme I can be made by the steps shown in Schemes II and III. Throughout Schemes II and III, W, X, Y, Z, $R^1$, $R^{14}$ and $R^{15}$ are as defined above, m is a metal atom (such as lithium atom) or a metal atom plus an associated halogen atom (such as MgI, MgBr or MgCl), and L is halogen atom (a bromine, iodine or chlorine atom).

Scheme II
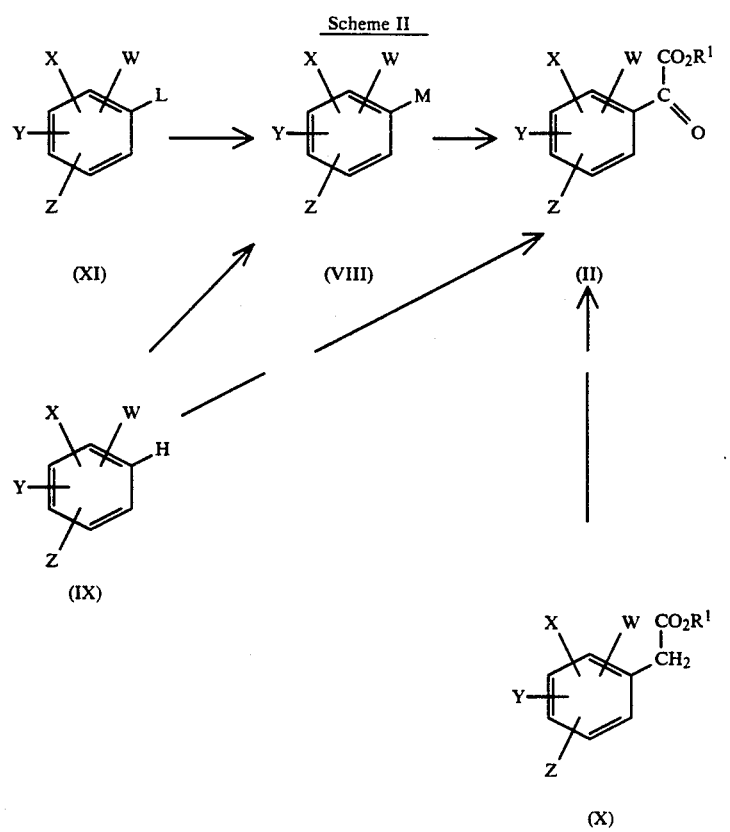
Scheme III
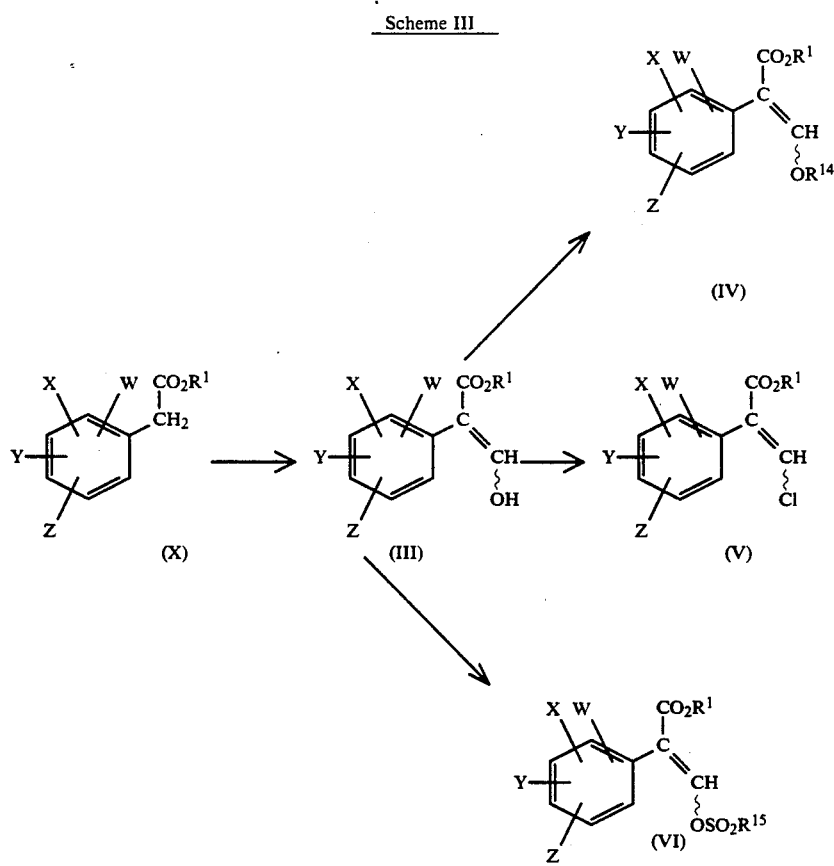

Thus ketoesters of formula (II) can be prepared by the following methods. Each transformation is often performed in a convenient solvent.

(i) By treatment of metallated species of formula (VIII) with an oxalate of formula $R^1O_2C.CO_2R^1$. The preferred method often involves slow addition of a solution of the metallated species (VIII) to a stirred solution of an excess of the oxalate (see, for example, L M Weinstock, R B Currie and A V Lovell, *Synth.Commun.*, 1981, 11, 943, and references therein). The metallated species (VIII) in which M is MgI, MgBr or MgCl (Grignard reagents) can be prepared from the corresponding halobenzenes (XI) in which L is I, Br or Cl respectively by standard methods. The metallated species (VIII) in which M is lithium can be prepared from the corresponding halobenzenes (XI) by metal-halogen exchange with, for example, n-butyl-lithium using standard methods. With certain substituents X, Y and Z, the metallated species (VIII) in which M is lithium can be prepared by direct lithiation of compounds (IX) using a strong lithium base such as n-butyl-lithium or lithium diisopropylamide (see, for example, H W Gschwend and H R Rodriguez, *Organic Reactions*, 1979, 26, 1).

(ii) By Friedel-Crafts acylation of substituted benzenes (IX) using, for example, an alkyl oxalyl chloride of formula $R^1O_2C.COCl$ in the presence of an acid, especially a Lewis acid, in catalytic or stoichiometric amounts.

(iii) By oxidation of phenylacetates of formula (X) using, for example, selenium dioxide.

Beta-alkoxyacrylates of formula (IV) can be made from enols of formula (III) under either acidic or basic conditions :

(i) Using an alcohol of formula $R^{14}OH$ and an acid, optionally with a dehydrating agent such as a trialkylorthoformate of formula $(R^{14}O)_3CH$. The alcohol may form the solvent for the reaction, or an additional inert solvent may be used.

(ii) Using a base (such as potassium carbonate or sodium hydride) and a species of general formula $R^{14}L$, in a suitable solvent.

Beta-chloroacrylates of formula (V) can be made from enols of formula (III) using a chlorinating reagent such as phosphorus pentachloride, often in a suitable solvent such as chlorinated hydrocarbon.

Beta-sulphonyloxyacrylates of formula (VI) can be made from enols of formula (III) using a sulphonyl chloride of formula $R^{15}SO_2Cl$, usually in the presence of a base such as triethylamine or pyridine, and usually in a suitable solvent.

Enols of formula (III) can be made by treatment of phenylacetates of formula (X) with a base (such as sodium hydride) and a formic ester of general formula $HCO_2R^1$, in a suitable solvent, and subsequent treatment with a mineral acid.

Halobenzenes of formula (XI), benzenes of formula (IX), and phenylacetates of formula (X) can be made by standard procedures described in the chemical literature.

In other aspects the invention provides processes as herein described for preparing the compounds of formula (I) and the intermediate chemicals of formulae (II)–(VII).

The compounds and metal complexes of the invention are active fungicides, and may be used to control one or more of the pathogens:

*Pyricularia oryzae* on rice *Puccinia recondita, Puccinia striiformis* and other rusts on wheat, *Puccinia hordei, Puccinia striiformis* and other rusts on barley, and rusts on other hosts eg. coffee, pears, apples, peanuts, vegetables and ornamental plants.

*Erysiphe graminis* (powdery mildew) on barley and wheat and other powdery mildews on various hosts such as *Sphaerotheca macularis* on hops, *Sphaerotheca fuliginea* on cucurbits (eg. cucumber), *Podosphaera leucotricha* on apples and *Uncinula necator* on vines. *Helminthosporium* spp., *Pseudocercosporella herpotrichoides* on cereals. *Cercospora arachidicola* and *Cercosporidium personata* on peanuts and other *Cercospora* species on other hosts for example sugar beet, bananas, soya beans and rice. Alternaria species on vegetables (eg. cucumber), oil seed rape, apples, tomatoes and other hosts. *Venturia inaequalis* (scab) on apples. *Plasmopara viticola* on vines. Other downy mildews such as *Bremia lactucae* on lettuce, Peronospora spp. on soybeans, tobacco, onions and other hosts and *Pseudoperonospora humuli* on hops and *Pseudoperonospora cubensis* on cucurbits. *Phytophthora infestans* on potatoes and tomatoes and other Phytophthora spp. on vegetables, strawberries, avocado, pepper, ornamentals, tobacco, cocoa and other hosts.

Some of the compounds show a broad range of activities against fungi in vitro.

They may also have activity against various postharvest diseases of fruit (eg. *Penicillium digitatum* and *italicum* and *Trichoderma viride* on oranges and *Gloeosporium musarum* on bananas). Further some of the compounds may be active as seed dressings.

The compounds may move locally in plant leaves or even move acropetally in the plant tissue. Moreover, the compounds may be volatile enough to be active in the vapour phase against fungi on the plant.

The compounds may also be useful as industrial (as opposed to agricultural) fungicides, eg. in the prevention of fungal attack on wood, hides, leather and especially paint films.

The compounds of the invention may have useful insecticidal activity against a range of insect species and nematodes, and may show knockdown activity against flies and mosquitoes. Therefore in a further aspect of the invention there is provided a method for killing or controlling insect or nematode pests which comprises administering to the pest or to a locus thereof an effective amount of an insecticidal/nematocidal compound of formula (I).

A preferred group of compounds for use in this aspect of the invention are compounds of formula (I) where one of W, X, Y or Z is substituted alkenyl, such as phenylethenyl.

A particularly preferred compound for use in this method is compound 9 in Table I.

Similarly, some compounds may exhibit plant growth regulating activity and may be deployed for this purpose at appropriate rates of application. Therefore in yet a further aspect of the invention there is provided a method of regulating plant growth which comprises applying to a plant an effective amount of a compound of formula (I).

This invention, therefore, includes the foregoing uses of the compounds (and compositions containing them) in addition to their principal use as fungicides.

The compounds may be used directly for fungicidal purposes but are more conveniently formulated into compositions using a carrier or diluent. The invention thus provides a fungicidal composition comprising a compound of general formula (I) as hereinbefore defined, and a fungicidally acceptable carrier or diluent.

The invention also provides a method of combating fungi, which comprises applying to a plant, to a seed of a plant, or to the locus of the plant or seed, a compound as hereinbefore defined, or a composition containing the same.

The compounds, can be applied in a number of ways. For example they can be applied, formulated or unformulated, directly to the foliage of a plant, to seeds or to other medium in which plants are growing or are to be planted. They can be sprayed on, dusted on or applied as a cream or paste formulation; or they can be applied as a vapour or as slow release granules. Application can be to any part of the plant including the foliage, stems, branches or roots, or to soil surrounding the roots, or to the seed before it is planted; or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example fillers such as kaolin, bentonite, kieselguhr, dolomite, calcium carbonate, talc, powdered magnesia, Fuller's earth, gypsum, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example a mineral oil) for assisting the adhesion of the composition to the seed; alternatively the active ingredient can be formulated for seed dressing purposes using an organic solvent (for example N-methylpyrrolidone, propylene glycol or dimethylformamide). The compositions may also be in the form of wettable powders or water dispersible granules comprising wetting or dispersing agents to facilitate their dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent and including a suspending agent to stop the solid settling.

Compositions to be used as sprays may be in the form of aerosols wherein the formulation is held in a container under pressure in the presence of a propellant, eg. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in a microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (eg. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants eg. a wetting agent, dispersing agent, emulsifying agent or suspending agent. These agents can be cationic, anionic or non-ionic agents.

Suitable cationic agents are quaternary ammonium compounds, for example cetyltrimethylammonium bromide. Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, eg. compounds having similar or complementary fungicidal activity or which possess plant growth regulating, herbicidal or insecticidal activity.

A fungicidal compound which may be present in the composition of the invention may be one which is capable of combating ear diseases of cereals (eg. wheat) such as Septoria, Gibberella and Helminthosporium spp., seed and soil borne diseases and downy and powdery mildews on grapes and powdery mildew and scab on apple etc. By including another fungicide the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are carbendazim, benomyl, thiophanate-methyl, thiabendazole, fuberidazole, etridazole, dichlofluanid, cymoxanil, oxadixyl, ofurace, metalaxyl, furalaxyl, 4-chloro-N-(cyanoethoxymethyl)benzamide, benalaxyl, fosetylaluminium, fenarimol, iprodione, prothiocarb, procymidone, vinclozolin, penconazole, myclobutanil, propamocarb, diconazole, pyrazophos, ethirimol, ditalimfos, tridemorph, triforine, nuarimol, triazbutyl, guazatine, triacetate salt of 1,1'-iminodi(octamethylene)diguanidine, buthiobate, propiconazole, prochloraz, flutriafol, hexaconazole ie. the chemical 1-(1,2,4-triazol-1-yl)-2-(2,4-dichlorophenyl)-hexan-2-ol, (2RS,3RS)-2-(4-chlorophenyl)-3-cyclopropyl-1-(1H-1,2,4-triazol-1-yl)butan-2-ol, (RS)-1-(4-chlorophenyl)-4,4-dimethyl-3-(1H-1,2,4-triazol-1-ylmethyl)pentan-3-ol, flusilazole, pyrifenox, triadimefon, triadimenol, diclobutrazol, fenpropimorph, fenpropidine, chlorozolinate, imazalil, fenfuram, carboxin, oxycarboxin, methfuroxam, dodemorph, BAS 454, blasticidin S, Kasugamycin, edifenphos, kitazin P, cycloheximide, phthalide, probenazole, isoprothiolane, tricyclazole, pyroquilon, chlorbenzthiazone, neoasozin, polyoxin D, validamycin A, mepronil, flutolanil, pencycuron, diclomezine, phenazin oxide, nickel dimethyldithiocarbamate, techlofthalam, bitertanol, bupirimate, etaconazole, hydroxyisoxazole, streptomycin, cyprofuram, biloxazol, quinomethionate, dimethirimol, 1-(2-cyano-2-methoxyiminoacetyl)-3-ethyl urea, fenapanil, tolclofos-methyl, pyroxyfur, polyram, maneb, mancozeb, captafol, chlorothalonil, anilazine, thiram, captan, folpet, zineb, propineb, sulphur, dinocap, dichlone, chloroneb, binapacryl, nitrothal-isopropyl, dodine, dithianon, fentin hydroxide, fentin acetate, tecnazene, quintozene, dichloran, copper containing compounds such as copper oxychloride, copper sulphate and Bordeaux mixture, and organomercury compounds. The compounds of general formula (I) can be mixed with soil, peat or other rooting media for the protection of plants against seed-borne, soil-borne or foliar fungal diseases.

Suitable insecticides which may be incorporated in the composition of the invention include pirimicarb, dimethoate, demeton-s-methyl, formothion, carbaryl, isoprocarb, XMC, BPMC, carbofuran, carbosulfan, diazinon, fenthion, fenitrothion, phenthoate, chlorpyrifos, isoxathion, propaphos, monocrotophas, buprofezin, ethroproxyfen and cycloprothrin.

Plant growth regulating compounds are compounds which control weeds or seedhead formation, or selectively control the growth of less desirable plants (eg. grasses).

Examples of suitable plant growth regulating compounds for use with the invention compounds are the gibberellins (eg. $GA_3$, $GA_4$ or $GA_7$), the auxins (eg. indoleacetic acid, indolebutyric acid, naphthoxyacetic acid or naphthylacetic acid), the cytokinins (eg. kinetin, diphenylurea, benzimidazole, benzyladenine or benzylaminopurine), phenoxyacetic acids (eg. 2,4-D or MCPA), substituted benzoic acids (eg. triiodobenzoic acid), morphactins (eg. chlorfluoroecol), maleic hydrazide, glyphosate, glyphosine, long chain fatty alcohols and acids, dikegulac, paclobutrazol, flurprimidol, fluoridamid, mefluidide, substituted quaternary ammonium and phosphonium compounds (eg. chloromequat chlorphonium or mepiquatchloride), ethephon, carbetamide, methyl-3,6-dichloroanisate, daminozide, asulam, abscisic acid, isopyrimol, 1-(4-chlorophenyl)-4,6-dimethyl-2-oxo-1,2-dihydropyridine-3-carboxylic acid, hydroxybenzonitriles (eg. bromoxynil), difenzoquat, benzoylprop-ethyl 3,6-dichloropicolinic acid, fenpentezol, inabenfide, triapenthenol and tecnazene.

The following Examples illustrate the invention. Throughout these Examples, the term "ether" refers to diethyl ether; magnesium sulphate was used to dry solutions; and reactions involving water-sensitive intermediates were performed under atmospheres of nitrogen. Unless otherwise stated, chromatography was performed using silica gel as the stationary phase. Where shown, infrared and nmr data are selective; no attempt is made to list every absorption. The following abbreviations are used throughout:

| | |
|---|---|
| THF = tetrahydrofuran | s = singlet |
| DMF = N,N-dimethylformamide | d = doublet |
| GC = Gas chromatography | t = triplet |
| MS = Mass spectrum | m = multiplet |
| mp = Melting point | delta = chemical shift |
| ml = milliliter(s) | $CDCl_3$ = deuterochloroform |
| mg = milligramme(s) | J = coupling constant |
| g = gramme(s) | Hz = Hertz |
| DMSO = dimethylsulphoxide | br = broad |
| $^1H$ NMR = Proton nuclear magnetic resonance | |

EXAMPLE 1

This Example illustrates the preparation of (E)-methyl 2-phenyl-3-(methylthio)propenoate (Compound No. 1 of Table I).

A solution of methyl phenylacetate (16.03g) in methyl formate (132ml) and dry DMF (100 ml) was added dropwise over 40 minutes to a stirred suspension of sodium hydride (5.14g) in dry DMF (200ml) at between 0° and 5° C. (effervescence and foaming). The resulting mixture was stirred at about −5° C. for 30 minutes, diluted with dry DMF (250ml), then allowed to warm and stir at room temperature for 3 hours. Ice and sodium carbonate were added to the mixture and it was washed with ether (x2), then acidified with concentrated hydrochloric acid and extracted with ether (x4). The extracts were washed with water (x3), treated with magnesium sulphate and charcoal, filtered and concentrated to give methyl 3-hydroxy-2-phenylpropenoate (13.56g, 71%) as a solid, m.p. 33.5°–35.5° C., which was used for the subsequent steps without further purification.

Phosphorus pentachloride (4.03g) was added in portions to a stirred solution of methyl 3-hydroxy-2-phenylpropenoate (2.65g) in dry dichloromethane (40ml), cooled in an ice-salt bath (effervescence). After 45 minutes, the cooling bath was removed and the resulting mixture was stirred at room temperature for 75 minutes then poured into water. The organic layer was separated and the aqueous layer was extracted with further dichloromethane. The combined organic layers were washed with aqueous potassium carbonate (x2) then with water (x3), dried and concentrated to give a pale yellow liquid (3.09g). This crude product, combined with similar crude material (227mg) from a previous small-scale pilot experiment, was chromatographed using 12% ether in hexane to give (E)-methyl 3-chloro-2-phenylpropenoate (1.83g, represents 58% yield) as a colourless mobile liquid, $^1$H NMR (CDCl$_3$) delta 3.79 (3H,s), 7.61 (1H,s) ppm.

A solution of sodium methanethiolate (96mg) in water (2ml) was added to a stirred solution of (E)-methyl 3-chloro-2-phenylpropenoate (236mg) in DMF (5ml), cooled in an ice-water bath. After 5 minutes, the cooling bath was removed and after 1.5 hours at room temperature the mixture was poured into water and extracted with ether. The extracts were washed with aqueous potassium carbonate (x2) then with water (x3), dried and concentrated to give the title compound (224mg, 86% yield) as a colourless oil (96% pure by GC, containing 2% of the corresponding (Z)-isomer), $^1$H NMR (CDCl$_3$) delta 2.42 (3H,s), 3.76 (3H,s), 7.82 (1H,s) ppm. On standing, the product crystallised to give a white solid, m.p. 49°-52° C. Recrystallisation from 40°-60° C. petrol gave colourless flakes, m.p. 54°-55° C., found : C,63.3; H,5.9%; C$_{11}$H$_{12}$O$_2$S requires C, 63.44; H, 5.81%.

EXAMPLE 2

This Example illustrates the preparation of (E)-methyl 2-(2-phenoxyphenyl)-3-(methylthio)propenoate (Compound No. 1 of Table II).

n-Butyl-lithium (77ml of a 2.6M solution in hexane) was added dropwise over 30 minutes to a stirred solution of diphenyl ether (34.0g) in dry ether (300ml), cooled to about 0° C. The resulting orange solution was stirred at room temperature for 3 hours, allowed to stand overnight, then added dropwise over 1.5 hours to a stirred solution of dimethyl oxalate (47.0g) in dry THF (200ml), cooled to just below 10° C. The resulting mixture was allowed to stand overnight, and was then poured into water and extracted with ether. The extracts were washed with water, dried, and concentrated under reduced pressure to give a brown oil (58.57g). Part of this oil (12.20g) was purified by column chromatography using 20% ether in petrol as eluant to give methyl o-phenoxybenzoylformate (5.87g, representing 55% yield) as a pale yellow oil.

Potassium t-butoxide (3.02g) was added in one portion to a stirred suspension of (methylthiomethyl)triphenylphosphonium chloride (11.26g) in dry ether (150ml). A bright yellow colour began to form immediately. After 40 minutes, a solution of methyl o-phenoxybenzoylformate (4.60g) in dry ether (20ml) was added rapidly, and the colour was discharged. After a further 3 hours, the reaction mixture was diluted with water and extracted with ether. The extracts were treated with magnesium sulphate and charcoal, filtered, concentrated under reduced pressure, and flushed through a short column of silica gel using ether to remove triphenylphosphine oxide, to give a pale yellow solid (4.56g). Trituration of this solid with petrol containing a little ether, then crystallisation of the resulting solid from dichloromethane and petrol, gave the title compound (1.01 g) as a pure white solid, m.p. 96-97½° C. An analytical sample, recrystallised from a mixture of ether and petrol, had m.p. 98-98½° C., infrared (nujol): 1705, 1569, 1234 cm$^{-1}$, $^1$H NMR (CDCl$_3$) : delta 2.40 (3H,s), 3.62 (3H,s), 7.77 (1H,s) ppm, Found : C, 67.9; H, 5.3%; C$_{17}$H$_{16}$O$_3$S requires C, 67.98; H, 5.37%. Chromatography of the combined mother liquors from the trituration and crystallisation described above using 15% ether in petrol gave recovered methyl o-phenoxybenzoylformate (1.46g) and a further batch of the title compound (0.76g after recrystallisation). The yield of the title compound, based on the recovered starting material, is 48%.

NOTE : Analysis of the crude product from the Wittig reaction described above using GC/MS indicated that the (Z)-isomer of the title compound was also present, but only in a small quantity. (E/Z)-Selectivity of the reaction was about 92:8. Other Wittig reactions of the same kind were sometimes less selective, allowing (Z)-isomers to be isolated. For example, the reaction using methyl benzoylformate gave compounds 1 and 2 of Table I in a ratio of ca. 2:1 respectively.

EXAMPLE 3

This Example describes the preparation of (E)-methyl 2-([2-(2-furyl)ethyl]phenyl)-3-(methylthio)propenoate (Compound No. 97 of Table I).

Methyl 2-methylbenzoate was treated successively with N-bromosuccinimide in chloroform and triphenylphosphine in toluene to give (o-methoxycarbonylbenzyl)triphenylphosphonium bromide as a white solid, mp. 230°-234° C., $^1$H NMR (D$_6$-DMSO) delta 3.36 (3H,s); 5.47 (2H, br d J 17 Hz) ppm.

1,8-Diazabicyclo[5.4.0]undec-7-ene (10.72g) was added to a stirred solution of (o-methoxycarbonylbenzyl)triphenylphosphonium bromide (45g) in dry dichloromethane (ca. 760 ml) to give an orange-red reaction mixture. After 20 minutes, a solution of furfural (5.56g) in dichloromethane (ca. 40 ml) was added and the colour was discharged. The resulting mixture was stirred at room temperature for 1.5 hours, then diluted with water. The aqueous and organic layers were separated, and the latter was washed successively with aqueous sodium bicarbonate (x2), brine and water, then dried and concentrated to give a yellow solid (46.77g). A solution of this solid in a mixture of ether and petrol was eluted through a short column of silica gel using a mixture of ether and petrol to remove triphenylphosphine oxide and excess starting phosphonium salt. The resulting material was chromatographed using 15% ether in petrol as eluant to give a 62:38 mixture of geometric isomers of methyl 2-[2-(2-furyl)ethenyl]benzoate (12.87g, 97% yield) as a pale yellow oil.

A solution of part of this ester (11.45 g) in ethyl acetate (70 ml) containing 10% w/w palladium on carbon (1.2g) was hydrogenated under a pressure of two atmospheres of hydrogen. Removal of the catalyst by filtration and concentration of the filtrate gave methyl 2-[2-(2-furyl)-ethyl]benzoate (11.18g, 96% yield) as a colourless liquid, $^1$H NMR (CDCl$_3$):delta 2.91-2.97 (2H,m), 3.23-3.39 (2H,m), 3.89 (3H,s), 5.96 (1H,m), 6.25 (1H,m), 7.15-7.42 (4H,m), 7.89 (1H,m) ppm.

Methyl 2-[2-(2-furyl)ethyl]benzoate was homologated to methyl 2-[2-(2-furyl)ethyl]phenylacetate in 4 steps:

(a) Reduction of the benzoate to the benzyl alcohol with lithiumaluminium hydride in ether;

(b) Conversion of the benzyl alcohol into the corresponding benzyl chloride using thionyl chloride and triethylamine in dichloromethane;

(c) conversion of the benzyl chloride into the corresponding phenylacetic acid by formation of a Grignard reagent in ether and treatment of it with carbon dioxide; and (d) Esterification of the phenylacetic acid using potassium carbonate and dimethyl sulphate in DMF. Methyl 2-[2-(2-furyl)ethyl]phenylacetate is an oil, $^1$H NMR, (CDCl$_3$, 60 MHz); delta 2.97 (4H,br s); 3.68 (5H,br s); ppm.

A solution of methyl 2-[2-(2-furyl)ethyl]phenyl acetate (2.27g) in methyl formate (5.7 ml) and dry DMF (ca. 10 ml) was added dropwise to a stirred suspension of sodium hydride (0.938g) in dry DMF (ca. 40 ml) cooled in an ice bath to about 0° C. (effervescence). Following the addition, the reaction mixture was allowed to warm to room temperature and was stirred for 3.5 hours. Water was then added to the mixture, and it was acidified with hydrochloric acid and extracted with ether. The extracts were washed with water, dried and concentrated to give a pale yellow gum (1.62g). Triethylamine (0.29 ml) and, after 5 minutes, methanesulphonyl chloride (0.21 ml), were added successively to a stirred solution of part of this gum (0.65g) in dry dichloromethane (10 ml). After an hour, dry DMF (10 ml) and sodium methanethiolate (0.202g) were added successively to the reaction mixture which was then stirred for 4 hours. The mixture was diluted with water and extracted with ether. The extracts were washed with water, dried, concentrated and chromatographed to give the title compound (0.303g, 27% yield from the phenylacetate) as a gum, $^1$H NMR (CDCl$_3$) delta 2.72–2.90 (4H,m), 3.04 (3H,s), 3.78 (3H,s), 5.95 (1H,d), 6.26 (1H,m), 7.08 (1H,d), 7.2–7.35 (4H,m), 7.99 (1H,s) ppm.

EXAMPLE 4

This Example illustrates the preparation of (E)-methyl 2-(2-[2-(4-fluorophenyl)ethyl]phenyl)-3-(methylthio)propenoate (Compound No. 96 of Table I).

Methyl 2-(2-[4-fluorophenyl]ethyl)phenylacetate was prepared from 4-fluorobenzaldehyde and (o-methoxycarbonylbenzyl)triphenylphosphonium bromide by a route similar to that described in Example 3 for the preparation of methyl 2-[2-(2-furyl)ethyl]phenylacetate. In this instance, the benzyl chloride was converted into the phenylacetate by treatment with potassium cyanide in DMSO and, then, methanolysis of the resulting phenylacetonitrile with sulphuric acid in methanol.

A solution of methyl 2-(2-[4-fluorophenyl]ethyl)phenylacetate (2.83g) and methyl formate (12.8ml) in dry DMF (20ml) was added dropwise over 20 minutes to a stirred suspension of sodium hydride (0.50g) in dry DMF (30ml) cooled in an ice bath. Effervescence and foaming built up slowly, and, when it had subsided, the mixture was allowed to warm to room temperature and stir for 3.5 hours. The mixture was diluted with water, acidified with concentrated hydrochloric acid and extracted with ether. The extracts were washed with water, dried and concentrated. A stirred solution of the resulting viscous yellow oil (3.34g) in DMF (30ml) was treated successively with potassium carbonate (3.05g) and dimethyl sulphate (1.54g). After 2 hours, the reaction mixture was poured into water and extracted with ether. The extracts were washed with water, dried, concentrated and chromatographed using 30% ether in petrol to give (E)-methyl 2-(2-[2-(4-fluorophenyl)ethyl]phenyl)-3-methoxypropenoate (2.64g, 81% yield) as a colourless solid m.p. 41½°–42½° C., $^1$H NMR (CDCl$_3$); delta 2.76 (4H,br s), 3.70 (3H,s), 3.82 (3H,s), 7.58 (1H,s), ppm.

Methane thiol (2ml) was condensed into an acetone dry ice trap. This was then allowed to warm and bubble into a stirred solution of (E)-methyl 2-(2-[2-(4-fluorophenyl)ethyl]phenyl)-3-methoxypropenoate (1.22g) in dry dichloromethane (20ml) containing a catalytic amount of 4-toluenesulphonic acid, in a flask fitted with a dry-ice condenser. The resulting mixture was stirred at room temperature for 2 hours, then heated under reflux of the dichloromethane for 6 hours, then allowed to cool. Aqueous sodium bicarbonate was added and the organic layer was separated, washed with water (x2), dried, concentrated and chromatographed using 30% ether in petrol to give methyl 2-(2-[2-(4-fluorophenyl)ethyl]phenyl)-3,3-di-(methylthio)propanoate (423mg, 34% yield based on recovered starting material) as a colourless glass, $^1$H NMR (CDCl$_3$) delta 1.98 (3H,s), 2.21 (3H,s), 2.85-3.05 (4H,m), 3.72 (3H,s), 4.24 (1H, d J 13Hz), 4.41 (1H, d J 13Hz) ppm. Recovered (E)-methyl 2-(2-[2-(4-fluoro-phenyl)ethyl]phenyl)3-methoxypropenoate (191mg) and a trace of the title compound were also isolated.

Titanium tetrachloride (0.12ml) and, after 10 minutes, triethylamine (0.16ml) were added successively to a stirred solution of methyl 2-(2-[2-(4-fluorophenyl)ethyl]phenyl)-3,3-di(methylthio)propanoate (350mg) in dry dichloromethane, cooled to −40° C. The resulting mixture was stirred at −40° C. for 20 minutes, then allowed to warm to room temperature, washed with water (x2), dried and concentrated to give a pale yellow glass (292mg). GC analysis showed that a comparatively volatile impurity was present and this was removed by heating at 140° C. and 0.01 mmHg, the residue then being chromatographed using 15% ether in petrol to give the title compound (239mg, 95% pure by GC, 73% yield) as a viscous oil, $^1$H NMR (CDCl$_3$): delta 2.40 (3H,s), 2.7–2.9 (4H,m), 3.72 (3H,s), 7.90 (1H,s) ppm.

The following are examples of compositions suitable for agricultural and horticultural purposes which can be formulated from the compounds of the invention. Such compositions form another aspect of the invention. Temperatures are given in degrees centigrade (° C.): percentages by weight.

EXAMPLE 5

An emulsifiable concentrate is made up by mixing the ingredients, and stirring the mixture until all the constituents are dissolved.

| | |
|---|---|
| Compound of Example 2 | 10% |
| Benzyl alcohol | 30% |
| Calcium dodecylbenzenesulphonate | 5% |
| Nonylphenolethoxylate (13 moles ethylene oxide) | 10% |
| Alkyl benzenes | 45% |

EXAMPLE 6

The active ingredient is dissolved in methylene dichloride and the resultant liquid sprayed onto the granules of attapulgite clay. The solvent is then allowed to evaporate to produce a granular composition.

| Compound of Example 2 | 5% |
|---|---|
| Attapulgite granules | 95% |

EXAMPLE 7

A composition suitable for use as a seed dressing is prepared by grinding and mixing the three ingredients.

| Compound of Example 2 | 50% |
|---|---|
| Mineral oil | 2% |
| China clay | 48% |

EXAMPLE 8

A dustable powder is prepared by grinding and mixing the active ingredient with talc.

| Compound of Example 2 | 5% |
|---|---|
| Talc | 95% |

EXAMPLE 9

A suspension concentrate is prepared for chemicals which are largely insoluble solids by ball milling, for example, the constituents set out below, to form an aqueous suspension of the ground mixture with water.

| Compound of Example 2 | 40% |
|---|---|
| Sodium lignosulphonate | 10% |
| Bentonite clay | 1% |
| Water | 49% |

This formulation can be used as a spray by diluting into water or applied directly to seed.

EXAMPLE 10

A wettable powder formulation is made by mixing together the ingredients set out below and then grinding the mixture until all are thoroughly mixed.

| Compound of Example 2 | 25% |
|---|---|
| Sodium lauryl sulphate | 2% |
| Sodium lignosulphonate | 5% |
| Silica | 25% |
| China clay | 43% |

EXAMPLE 11

The compounds were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed on to the foliage and applied to the roots of the plants in the soil. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on Erysiphe graminis in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:
4 = no disease
3 = trace - 5% of disease on untreated plants
2 = 6-25% of disease on untreated plants
1 = 26-59% of disease on untreated plants
0 = 60-100% of disease on untreated plants
The results are shown in Table V.

TABLE V

| COMPOUND NO | TABLE | PUCCINIA RECONDITA (Wheat) | ERYSIPHE GRAMINIS (Barley) | VENTURIA INAEQUALIS (Apple) | PYRICULARIA ORYZAE (Rice) | CERCOSPORA ARACHIDICOLA (Peanut) | PLASMOPARA VITICOLA (Vine) |
|---|---|---|---|---|---|---|---|
| 1 | I | 0 | 0 | 0 | 1 | 0 | 0 |
| 2 | I | 0 | 0 | 0 | 0 | 0 | 1 |
| 9 | I | 3 | 0 | 4 | 4 | 1 | 0 |
| 10 | I | 2 | 0 | 4 | 3 | 4 | 4 |
| 96 | I | 0 | 0 | 3 | 0 | 0 | 0 |
| 1 | II | 4 | 3 | 4 | 2 | 0 | 4 |

EXAMPLE 12

This Example illustrates the insecticidal properties of the compound 9 in Table I.

The activity of the compound was determined using a variety of insect, mite and nematode pests. The compound was used in the form of liquid preparations containing from 100 to 500 parts per million (ppm) by weight of the compound. The preparations were made by dissolving the compound in acetone and diluting the solutions with water containing 0.1% by weight of a wetting agent sold under the trade name "SYNPERONIC" NX until the liquid preparations contained the required concentration of the product. "SYNPERONIC" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to seven days after the treatment.

The results of the tests are given in Table VII for each of the products, at the rate in parts per million given in the second column as a grading of mortality designated as 9, 5 or 0 wherein 9 indicates 80-100% mortality (70-100% root knot reduction as compared to an untreated plant for *Meloidogyne incognita*), 5 indicates 50-79% mortality (50-69% root knot reduction for *Meloidogyne incognita*) and 0 indicates less than 50% mortality (root knot reduction for *Meloidogyne incognita*).

In Table VII the pest organism used is designated by a letter code and the pests species, the support medium or food, and the type and duration of test is given in Table VI.

The knockdown properties of compound 9 in Table I against *Musca domestica* was demonstrated as follows.

A sample of compound 9 was diluted in 2 mls acetone and made up to a 2000 ppm solution with 0.1% aqueous synperonic solution. The solution (1 ml) was then sprayed directly onto twenty mixed sex houseflies held in a drinking cup. Immediately after spraying the cups were inverted and left to dry. An assessment of knockdown was made when the cups were righted 15 minutes later. The flies were then provided with a 10% sucrose solution on a cotton wool pad, and held for 48 hours in a holding room conditioned at 25° C. and 65% relative humidity before a mortality assessment was made.

Compound 9 under these conditions demonstrated 88% knockdown and 15% kill.

TABLE VI

| CODE LETTERS | TEST SPECIES | SUPPORT MEDIUM/ FOOD | TYPE OF TEST | DUR- ATION |
|---|---|---|---|---|
| TUa | *Tetranychus urticae* (spider mites - adult) | French bean leaf | Contact | 3 |
| TUe | *Tetranychus urticae* (spider mites - ova) | French bean leaf | Contact | 6 |
| MP | *Myzus persicae* (aphids) | Chinese cabbage leaf | Contact | 3 |
| NL | *Nilaparvata lugens* (brown plant hopper - nymphs) | Rice plant | Contact | 3 |
| HV | *Heliothis virescens* (tobacco budworm - larvae) | Cotton leaf | Residual | 3 |
| DB | *Diabrotica balteata* (rootworm larvae) | Filter paper/ maize seed | Residual | 3 |
| BG | *Blattella germanica* (cockroach nymphs) | Plastic pot | Residual | 3 |
| MD | *Musca domestica* (houseflies - adults) | Cotton wool/ sugar | Contact | 1 |
| SP | *Spodoptera exigua* (lesser army worm - larvae) | Cotton leaf | Residual | 3 |
| MI | *Meloidogyne incognita* (tomato root knot eelworm - larvae) | Semi in-vitro | Residual | 7 |

"Contact" test indicates that both pests and medium were treated and "residual" indicates that the medium was treated before infestation with the pests.

TABLE VII

| Compound No. | Rate (ppm) | TU$_A$ | TU$_E$ | MP | NL | MD | BG | HV | SP | DB | MI* |
|---|---|---|---|---|---|---|---|---|---|---|---|
| 9 | 500 | 0 | 0 | 0 | 0 | 5 | 0 | 0 | 0 | 5 | — |
| of Table I | 125 | — | — | — | — | — | — | — | — | — | 9 |

EXAMPLE 13

This Example illustrates the plant growth regulating Properties of compounds 1, 2, 9, 10 and 96 of Table I and compound 1 of Table II.

These compounds were tested on a whole plant screen for plant growth regulating activity against six species of plant. The plant species used in this screen are presented in Table VIII with the leaf stage at which they were sprayed.

A formulation of each chemical was applied at 4000 ppm (4 kg/ha in a 1000 l/ha field volume) using a track-sprayer and a SS8004E (Teejet) nozzle. Additional tests were done on tomatoes at 2000 and 500 ppm.

After spraying, the plants were grown in a glasshouse with 25° C. day/22° C. night temperatures. The exception to this were the temperate cereals, wheat and barley which were grown in 13°-16° C. day/11°-13° C. night temperatures. Supplementary lighting was supplied when necessary to provide an average photoperiod of 16 hours (14 hours minimum).

After 2-6 weeks in the glasshouse, depending on species and time of year, the plants were visually assessed for morphological characteristics against a control plant sprayed with a blank formulation. The results are presented in Table IX.

TABLE VII

| PLANT MATERIAL USED FOR WHOLE PLANT SCREEN | | | | | |
|---|---|---|---|---|---|
| Species | Code | Variety | Growth Stage at Treatment | No. Plants per 3" pot | Compost Type* |
| Barley | BR | Atem | 1-1.5 leaves | 4 | JIP |
| Wheat | WW | Timmo | 1-1.5 leaves | 4 | JIP |
| Maize | MZ | Earliking | 2½-2¼ leaves | 1 | PEAT |
| Apple | AP | Red Delicious | 4-5 leaves | 1 | JIP |
| Rice | RC | Ishikari | 2-2¼ leaves | 4 | JIP |
| Tomato | TO | Ailsa Craig | 2-2¼ leaves | 1 | PEAT |

*JIP = John Innes Potting Compost.

TABLE IX

| Compound No. | Table | BR | WW | RC | AP | MZ | TO | TO* | TO+ |
|---|---|---|---|---|---|---|---|---|---|
| 1 | I | | | 2 | | | NT | 1 | 1 |
| 2 | I | | | 1 | | | NT | 1G | 2G |

TABLE IX-continued

| Compound No. | Table | BR | WW | RC | AP | MZ | TO | TO* | TO+ |
|---|---|---|---|---|---|---|---|---|---|
| 9 | I | | | | | | | 3GAT | 2GAT |
| 10 | I | | | | | | NT | NT | NT |
| 96 | I | NT | | NT | NT | GA | | 1 | 2G |
| 1 | II | NT | 1 | NT | NT | | NT | 1 | 1G |

KEY
*2000 ppm
+500 ppm
Retardation 1-3 where 1 = 10-30%
2 = 21-60%
3 = 61-100%
Greening effect = G
Apical damage = A
Tillering or side shooting = T
Blank means less than 10% effect
NT indicates that the compound was not tested against this species
MJH/jlc
PP 33838
10 March 87

We claim:

1. A compound of the formula (I):

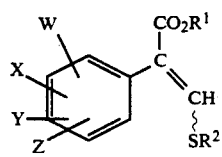

or stereoisomers thereof, wherein $R^1$ and $R^2$, which are the same or different, are methyl or methyl substituted with fluorine; W, X, Y and Z, which are the same or different, are hydrogen, halogen, hydroxy, alkyl, alkyl substituted with alkylthio, phenylthio or tetrahydropyranyl, cycloalkyl, cycloalkylalkyl, aralkyl, aryloxyalkyl, alkenyl, aryl, alkynyl, —NR'R", arylazo, heteroarylalkyl, heteroaryloxyalkyl, —NHCOR', nitro, cyano, —OR$^3$, —SR$^3$, —CO$_2$R$^4$, —CONR$^5$R$^6$, —COR$^7$, —CR$^8$=NR$^9$, —N=CR$^{10}$R$^{11}$, —SOR$^{12}$ or —SO$_2$R$^{13}$, or any two or W, X, Y and Z in adjacent positions on the phenyl ring, a fused benzene, naphthalene or benzofuran ring; R' and R" have the meanings given below; $R^3$ is alkyl, alkyl substituted with alkylthio or phenylthio, cycloalkyl, cycloalkyl containing a hetero atom in the cyclo-alkyl ring, alkenyl, aryl, aralkyl, —COR', or heteroaryl; $R^4$, $R^5$, $R^6$, $R^7$, $R^8$, $R^{10}$ and $R^{11}$, which are the same or different, are hydrogen, alkyl, cycloalkyl, cycloalkylalkyl, alkenyl, alkynyl, aryl, heteroaryl, aralkyl, or cycloalkylalkyl; and $R^9$, $R^{12}$ and $R^{13}$ are aryl or heteroaryl; wherein any of the foregoing alkyl groups and the alkyl moieties of alkoxy groups is unsubstituted or substituted with hydroxy, halogen or alkoxycarbonyl, any of the foregoing alkyl moieties of aralkyl and aryloxyalkyl groups is unsubstituted or substituted with hydroxy, any of the foregoing alkenyl groups is unsubstituted or substituted with aryl or heteroaryl or the terminal carbon atom of such groups forms part of a 5- or 6-membered cycloalkyl group, any of the foregoing alkynyl groups is unsubstituted or substituted with aryl, and wherein the aryl or heteroaryl moieties of any of the foregoing are unsubstituted or substituted with one or more of the following; halogen, hydroxy, C$_{1-4}$ alkyl, C$_{1-4}$ alkoxy, halo(C$_{1-4}$) alkyl, halo(C$_{1-4}$) alkoxy, C$_{1-4}$ alkylthio, C$_{1-4}$ alkoxy (C$_{1-4}$) alkyl, C$_{3-6}$ cycloalkyl, C$_{3-6}$ cycloalkyl (C$_{1-4}$)alkyl, aryl, aryloxy, aryl(C$_{1-4}$) alkyl, aryl(C$_{1-4}$) alkoxy, aryloxy(C$_{1-4}$) alkyl, carbacyl, cyano, thiocyanato, nitro, —NR'R", —NHCOR', —NHCONR''', —CONR'R", —COOR", —OSO$_2$R', —SO$_2$R', —COR', —CR'=NR" or —N=CR'R" in which R' and R" are independently hydrogen, C$_{1-4}$ alkyl, C$_{1-4}$ alkoxy, C$_{1-4}$ alkylthio, C$_{3-6}$ cycloalkyl, C$_{3-6}$ cycloalkyl (C$_{1-4}$) alkyl, phenyl or benzyl, the phenyl and benzyl groups being unsubstituted or substituted with halogen, C$_{1-4}$ alkyl or C$_{1-4}$ alkoxy.

2. A compound having the formula (Ia):

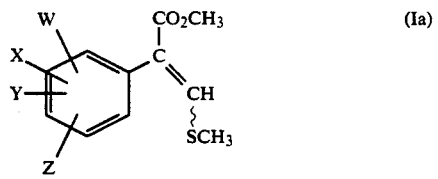

or stereoisomers thereof, wherein W, X, Y and Z, which are the same or different, are hydrogen, halogen, C$_{1-4}$ alkyl, C$_{1-4}$ alkyl substituted by hydroxy or C$_{1-4}$ alkoxycarbonyl, trifluoromethyl, phenyl (C$_{1-4}$) alkyl, phenoxy(C$_{1-4}$)alkyl, C$_{2-4}$ alkenyl, C$_{2-4}$ alkenyl substituted by an aromatic or heteroaromatic group which itself is unsubstituted or substituted with halogen, C$_{2-4}$ alkenyl in which the terminal carbon atom of the alkenyl group forms part of a 5-or 6-membered cycloalkyl group, C$_{2-4}$ alkynyl, C$_{2-4}$ alkynyl substituted with phenyl aryl, amino substituted by aryl or C$_{1-4}$ alkyl groups, arylazo, arylazo substituted by C$_{1-4}$ alkyl, C$_{1-4}$alkoxy or N,N-di(C$_{1-4}$)alkylamino, benzoylamino or furoylamino in which the amino moiety is unsubstituted or substituted with alkyl, nitro, —SR$^3$ or —OR$^3$ , in which R$^3$ is alkyl, alkyl substituted with alkylthio or phenylthio, or aralkyl in which the aryl group or the aryl moiety of the aralkyl group is unsubstituted or substituted with one or more of halogen, hydroxy, C$_{1-4}$ alkyl, C$_{1-4}$ alkoxy, trifluoromethoxy, phenoxy, nitro, amino, aryl(C$_{1-4}$)alkyl, phenyl, carboxy, alkoxycarbonyl, cyano, alkylcarbonylamino and methylenedioxy, heteroaryl, heteroaryl substituted with halogen, alkyl, trifluoromethyl, akloxy, trifluoromethoxy, nitro or amino, benzoyl, —SOR$^{12}$ or —SO$_2$R$^{13}$ in which R$^{12}$ and R$^{13}$ are aryl, —CO$_2$R$^4$ in which R$^4$ is alkyl, aryl, C$_{3-6}$ cycloalkyl, C$_{3-6}$ cycloalkyl(C$_{1-4}$)-alkyl or aryl(C$_{1-4}$)alkyl, —COR$^7$ in which R$^7$ is alkyl, aryl or methoxyphenyl, or any two of W, X, Y and Z, in adjacent positions on the phenyl ring, join to form a fused benzene, naphthalene or benzofuran ring.

3. A compound having the formula (Ib):

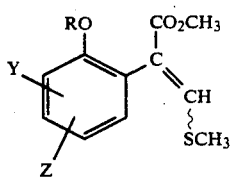

(Ib)

wherein R is hydrogen, $C_{1-4}$ alkyl, $C_{1-4}$ alkyl substituted by $C_{1-4}$ alkylthio, phenylthio or phenyl in which the phenyl group itself is unsubstituted or substituted by halogen, $C_{3-6}$ cycloalkyl, tetrahydropyranyl, $C_{2-4}$ alkenyl, $C_{2-4}$ alkenyl substituted with phenyl, phenyl, phenyl substituted by one or more of halogen, hydroxy, $C_{1-4}$ alkyl, $C_{1-4}$ alkoxy, trifluoromethoxy, phenoxy, nitro, amino, aryl($C_{1-4}$)alkyl, phenyl, carboxy, alkoxycarbonyl, cyano, $C_{1-4}$ alkylcarbonylamino or methylenedioxy, naphthyl, pyridinyl or pyrimidinyl in which the pyridinyl and pyrimidinyl moieties are unsubstituted or substituted by halogen, trifluoromethyl, nitro, $C_{1-4}$ alkyl, $C_{1-4}$ alkoxy, trifluoromethoxy or amino; and Y and Z, which are the same or different, are hydrogen, halogen, $C_{1-4}$-alkyl, $C_{1-4}$ alkoxy, $C_{1-4}$-alkylthio, trifluoromethyl, nitro, N,N-di($C_{1-4}$)alkylamino, or Y and Z together form a methylenedioxy group.

4. A compound having the formula (Ic):

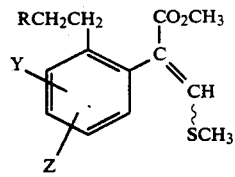

(Ic)

wherein R, Y and Z have the meanings given in claim 3 or R is also thienyl, furyl or pyrrolyl.

5. A compound having the formula (Id):

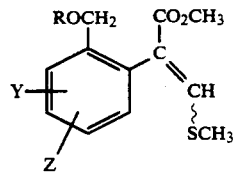

(Id)

wherein R, Y and Z have the meanings given in claim 4.

* * * * *